(12) United States Patent
Viola et al.

(10) Patent No.: US 11,111,488 B2
(45) Date of Patent: Sep. 7, 2021

(54) METHODS FOR EXTRACTING BIOACTIVE SMALL RNAS FROM PLANTS AND MUSHROOMS

(71) Applicant: MIRNAGREEN S.R.L., Rovereto (IT)

(72) Inventors: Roberto Viola, Rovereto (IT); Alfredo Maglione, Rovereto (IT)

(73) Assignee: MIRNAGREEN S.R.L., Rovereto (IT)

( * ) Notice: Subject to any disclaimer, the term of this patent is extended or adjusted under 35 U.S.C. 154(b) by 735 days.

(21) Appl. No.: 15/770,008

(22) PCT Filed: Oct. 28, 2016

(86) PCT No.: PCT/EP2016/076050
§ 371 (c)(1),
(2) Date: Apr. 20, 2018

(87) PCT Pub. No.: WO2017/072285
PCT Pub. Date: May 4, 2017

(65) Prior Publication Data
US 2020/0248171 A1    Aug. 6, 2020

(30) Foreign Application Priority Data

Oct. 28, 2015 (EP) .................................. 15191884

(51) Int. Cl.
*C12Q 1/68* (2018.01)
*C12N 15/10* (2006.01)

(52) U.S. Cl.
CPC .... *C12N 15/1006* (2013.01); *C12N 2310/141* (2013.01); *C12Q 2525/207* (2013.01); *C12Q 2600/178* (2013.01)

(58) Field of Classification Search
None
See application file for complete search history.

(56) References Cited

FOREIGN PATENT DOCUMENTS

| EP | 2345719 A1 | 7/2011 | | |
|---|---|---|---|---|
| WO | 9506652 A1 | 3/1995 | | |
| WO | 2005012523 A1 | 2/2005 | | |
| WO | 2007100934 A2 | 9/2007 | | |
| WO | 2007103485 A2 | 9/2007 | | |
| WO | WO-2007103485 A2 | * | 9/2007 | ......... C12N 15/1006 |
| WO | WO-2008074473 A2 | * | 6/2008 | ............ A23G 3/366 |
| WO | 2010033652 A1 | 3/2010 | | |
| WO | 2011086195 A1 | 7/2011 | | |
| WO | 2014033326 A1 | 3/2014 | | |

OTHER PUBLICATIONS

Peng et al.,"Rapid and Efficient Isolation of High-Quality Small RNAs from Recalcitrant Plant Species Rich in Polyphenols and Polysaccharides", PLOS ONE, 2014, vol. 9, Issue 5, e95687, 8 pages.
Rosas-Cardenas., "A simple and efficient method for isolating small RNAs from different plant species", Plant Methods, 2011, vol. 7. No. 1, pp. 1-7.
International Search Report and Written Opinion for International Application No. PCT/EP2016/076050 (12 Pages) (dated Dec. 13, 2016).

* cited by examiner

*Primary Examiner* — Stephanie K Mummert
(74) *Attorney, Agent, or Firm* — Lucas & Mercanti, LLP

(57) ABSTRACT

The present invention refers to a method for isolating a fraction enriched of small RNA molecules from a fungal or plant sample.

23 Claims, 9 Drawing Sheets

MRG sRNA extraction method (column)

Figure 1:
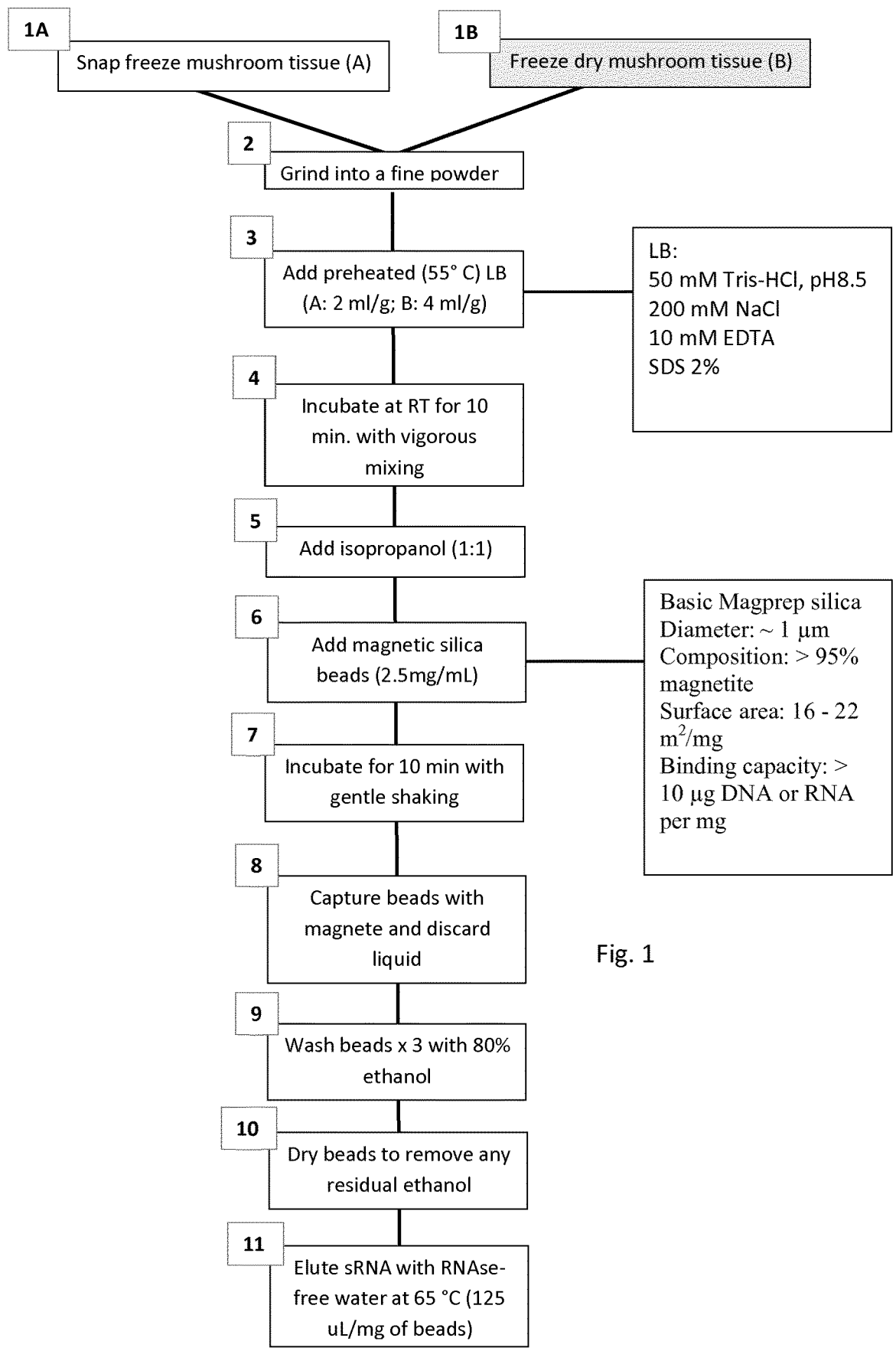

A.

B.

A.

B.

METHODS FOR EXTRACTING BIOACTIVE SMALL RNAS FROM PLANTS AND MUSHROOMS

CROSS-REFERENCE TO RELATED APPLICATIONS

This application is a 371 of PCT/EP2016/076050, filed Oct. 28, 2016, which claims the benefit of European Patent Application No. 15191884.4, filed Oct. 28, 2015.

TECHNICAL FIELD

The present invention relates to methods for isolating or extracting small RNA (sRNA) molecules from a fungal or plant sample. Said sRNAs comprise single stranded RNAs and/or single stranded RNAs with partial alignment but more preferably double stranded RNA with or without perfect sequence complementarity. The obtained sRNA may be used in food preparations and/or in the nutraceutical, cosmeceutical or pharmaceutical fields.

BACKGROUND OF THE INVENTION

WO2005012523 refers to the use of methods and compositions for the isolation of small RNA molecules (100 nucleotides or fewer), such as microRNA and siRNA molecules.

WO2011086195 refers to a method for isolating small RNA from a sample comprising binding the RNA to silica particles by contacting the sample with a) at least one alcohol, b) at least one chaotropic salt comprising a chaotropic anion selected from the group consisting of trichloroacetate, perchlorate and trifluoroacetate and c) silica particles and separating the bound RNA from the rest of the sample. Compositions and kits are also provided to efficiently isolate small RNA molecules from samples, in particular biological samples such as blood, blood products tissue and body fluids. WO2014033326 refers to a method for isolating RNA including small RNA having a size of 200 nt or less from a sample, comprising the following steps: a) providing a composition comprising RNA and a chaotropic agent; b) adding alcohol; c) incubating the mixture for at least 2 min; d) adding additional alcohol to the mixture to adjust the overall alcohol concentration in the mixture to>=50%; e) binding RNA contained in the mixture to a nucleic acid binding solid phase; f) optionally washing the bound RNA; g) optionally eluting RNA from the solid phase. Due to the step-wise addition of alcohol, the overall RNA yield and the yield of small RNA is improved.

WO2007100934 refers to extraction compositions and methods for the rapid and efficient isolation of small RNA molecules from a biological sample. In particular, the extraction compositions, when contacted with a biological sample, releases the small RNA molecules from the other molecules in a biological sample, and the released small RNA molecules may then be isolated.

WO2010033652 refers to a method for the extraction and purification of small RNA from a sample solution. Accordingly, a sample is first mixed with an organic solvent to form a mixture containing the solvent. The mixture is applied to a first mineral support for large RNA to bind. The filtrate is collected which contain unbound small RNA, and is mixed with a second organic solvent to form a second mixture containing the second solvent. This second mixture is applied to a second mineral support for small RNA to bind. After a wash step, the small RNA is eluted. Also provided is a method for the isolation of large RNA, by eluting the large RNA from the first mineral support. In addition, total protein is present in the filtrate and can be isolated by a conventional method. WO9506652 refers to compositions and methods for isolating nucleic acids with lengths greater than about 50 bases, from cells, gels, solutions and other media, in which nucleic acids occur in vivo or in vitro. The compositions of the invention are mixtures of the silica materials silica gel and glass particles, particularly glass microfibers; such mixtures combined with chaotropic salts, such as guanidinium chloride or guanidinium thiocyanate; and suspensions of such mixtures in aqueous solutions of chaotropic salts. In the methods of the invention, an aqueous solution comprising nucleic acid is mixed with an aqueous solution of chaotropic salts and the resulting solution is contacted with a mixture of the silica materials, whereupon the nucleic acid in the solution binds to the silica materials. The chaotropic salts and components, other than the nucleic acid adsorbed to the silica materials, from the aqueous solution treated by the method of the invention are washed from the silica materials. Finally, the nucleic acid can be obtained by elution from the silica materials. The methods provide nucleic acid in water or buffer, such as TE buffer, free of contamination by any salt or macromolecule that would interfere with further processing or analysis.

WO2007103485 relates to methods, kits, and compositions for purifying small RNA molecules. In particular, the present invention provides methods for purifying small RNA molecules from a sample containing both small RNA molecules and larger RNA molecules using a compaction agent and a RNA binding matrix, as well as compositions and kits for practicing such methods. In certain embodiments, the compaction agent comprises a plurality of metal-amine-halide molecules.

All known methods for isolation of small RNA from plants or mushrooms have been developed mainly for analytical scopes and are not suitable for efficient and isolation of safe small RNA molecules from fungi and/or plants which may be used in food industry. Thus they generally are employed with small amounts of tissues (mg or grams) and aim at providing the full spectrum of RNA species present in the tissue. This involves the use of chemical and physical strategies to prevent RNAse-mediated degradation of some types or RNAs most significantly mRNAs and other ssRNAs. The strategies used to prevent RNAse activity in the sample include the use of toxic solvents agents (i.e. phenol), solvents (chloroform) or chaotropic agents (TFA, PCA and guanidine HCl). All these methods are cumbersome and not amenable for scale-up or industrialization through the need for phase separation, centrifugation and/or the use (and disposal) of expensive or toxic solvents or reagents. In view of the non-sequence dependent immunomodulant activity of sRNA species recently demonstrated (*Plant microrna as novel immunomodulatory agents. Sci. Rep.* 2016, 6:25761, Cavalieri et al.), there is a need to perfect a method for extraction and isolation of sRNAs from high quantities plant or fungi tissues and which is designed to obtain maximum extraction particularly of the dsRNA species (20-60 bp length) which are responsible for the immunomodulant activity of sRNA extracts (*Plant microrna as novel immunomodulatory agents. Sci. Rep.* 2016, 6:25761, Cavalieri et al.). Moreover, such method should not involve the use of toxic or costly solvents and ideally do not contain complex technical steps (i.e. high speed centrifugation) that render it unsuitable or too expensive for scale-up.

SUMMARY OF THE INVENTION

The method for isolating a fraction enriched of small RNA (sRNA) molecules from a fungal or plant sample object of the present invention successfully allows to obtain over 100 mg of sRNA from a Kg of plant or mushroom tissue. The sRNA extract can then be further treated with RNAses to selectively remove ssRNA species and treated with a protein containing dsRNA binding domain which selectively recognizes dsRNA of between 21 to 24 bp to selectively purify the dsRNA species of 21 and 24 base pairs. The final extract can be safely used as a dietary supplement or for the nutraceuticals, pharmaceutical or cosmeceuticals industry.

It is therefore an object of the invention a method for isolating a fraction enriched of small RNA molecules from a fungal and/or plant sample comprising:
a) adding a lysis buffer to a powder or homogenized sample of fungal and/or plant tissue or cells sample to obtain a lysate; or
a') incubating fungal and/or plant tissue or cells with a bicarbonate solution at a temperature of 50-100° C., separate liquid from solid phase to obtain a liquid phase and
b) adding an alcohol solution to the lysate obtained is step a) or to the liquid phase obtained in step a') to obtain a solution;
c) loading the obtained solution to a solid support able to bind small RNA molecules;
d) eluting small RNA molecules from said solid support.

Said homogenized or powder sample is preferably obtained by homogenizing fungal and/or plant tissue or cells to obtain a powder or an homogenized sample or is a lyophilized powder.

Before homogenizing fungal and/or plant tissue or cells, the fungi or plant tissue or cells are preferably snap frozen or freeze dried.

In the method according to the invention, the ratio w/v between powder and lysis buffer in step a) is preferably of 1:1 to 1:4, preferably of 1:2.

Preferably, in the method according to the invention, the lysis buffer comprises:
a) 10-100 mM of Tris-HCl at a pH of 5-10, preferably 50 mM of Tris-HCl at a pH of 8-8.5,
b) 100-500 mM, preferably 100-300 mM, more preferably 200 mM, of NaCl,
c) EDTA 5-50 mM, preferably EDTA 10-20mM, more preferably EDTA 10mM,
d) SDS 0.5-10% (w/v), preferably SDS 2-4% (w/v), more preferably SDS 2% (w/v).

In a preferred embodiment the lysis buffer comprises: 50 mM Tris-HCl (pH 8.5), 200 mM NaCl, 10 mM EDTA and 2% SDS (w/v).

The bicarbonate solution is a preferably a diluted sodium bicarbonate solution, more preferably a 5-100 mM $NaHCO_3$ solution, even more preferably a 30 mM $NaHCO_3$. Other bicarbonate solutions may be alkali metal bicarbonate, preferably selected from the group consisting of sodium bicarbonate, potassium bicarbonate, and mixtures thereof.

The method of the invention may further comprise after step a'), a step a'') wherein the liquid phase is discarded and a diluted bicarbonate solution is added at a temperature of 60-100° C. and wherein the diluted bicarbonate solution is a 5-10 mM $NaHCO_3$, solution, preferably a 8.75 mM $NaHCO_3$ solution, said step a'') being optionally repeated.

The liquid may be separated from the solid phase and then be subjected to the addition of isopropanol.

The temperature of the diluted bicarbonate is preferably of about 95, 100 or 60° C.

Before step a') fungal and/or plant tissue or cells is preferably incubated with a diluted bicarbonate solution at 0-10° C., preferably at 4° C., wherein the diluted bicarbonate solution is a 5-10 mM $NaHCO_3$, solution, preferably a 8.75 mM $NaHCO_3$, solution. The incubation may be 10-20 h long, preferably 16 h. The liquid phase is then discarded. The starting plant or mushroom tissue may be intact or coarsely chopped.

In the method according to the invention the alcohol is preferably isopropanol, ethanol or any alcohol able to reduce the activity of water and therefore the solvation of sRNAs and promote their binding to the solid support.

More preferably, the alcohol solution comprises isopropanol at a final concentration of 60% v/v.

Preferably, the small RNA molecules are eluted from the solid support with RNAse-free water.

In a preferred embodiment of the invention, the small RNA molecules are eluted from the solid support at a temperature of about 50° C. to about 100° C., preferably at 55 or 65° C.

Preferably, the solid support is a mineral support or polymer support.

More preferably the mineral support or polymer support is a column comprising silica or silica gel or silicon dioxide particles.

More preferably the mineral or polymer support is a set of beads made of an absorptive polymer, preferably silica beads.

The set of beads are preferably collected by centrifugation, filtration, or magnetic capture.

The method according to the invention may further comprise capturing the eluted small RNA molecules. In some embodiments e.g. the sample is subsequently filtered after passage through a capture structure. The capture step can include filtration using a pressure-driven system or gravity-based system (for example, centrifugation).

In another embodiment, the method further comprises:
step e) selectively removing ssRNAs with RNAse treatment from the eluted small RNA molecules and/or
step f) treating the eluted small RNA molecules with an agent which binds with high affinity to siRNA duplexes of selectively 21-25 nt, to enrich the 21-24 bp dsRNA fraction. Preferably said agent is p19.

In step e) it may be used RNAse A or any RNAse able to completely degrade ssRNA. Preferably, the small RNA molecules (and the fraction enriched of small RNA molecules) include miRNA, siRNA, snRNA, snoRNA, and/or tRNA molecules, more preferably the small RNA molecules consist of at most 100 nucleotides, preferably at most 70 nucleotides, or more preferably at most 30 nucleotides.

The small RNA molecules preferably consist of between 21 and 24 nucleotide, more preferably between 19 and 24 nucleotides.

Said small RNA molecules are preferably in the single stranded and/or double stranded configurations.

Said small RNA molecules are preferably characterized by the presence of a phosphate group at the 5' ends and/or a methyl group at the 3' ends. The small RNA molecules are preferably miRNA, mature miRNA and/or siRNA molecules.

Another object of the invention is small RNA molecules obtained by the method as above defined. Further objects of the invention are a food and/or food additive and/or dietary supplement and/or a nutraceutical product comprising the small RNA molecules obtainable with the method as above defined, a method for producing a second food and/or a nutraceutical product comprising the addition to a first food and/or nutraceutical product of the small RNA molecules obtained by above method of the invention.

Another object of the invention is a pharmaceutical or cosmetic composition comprising the small RNA molecules obtainable with the method as above defined.

The pharmaceutical or cosmetic composition as above defined, the food and/or food additive and/or dietary supplement and/or a nutraceutical product as above defined, preferably comprise: a) lipids, more preferably at least one liposome, b) an exosome, c) a polymeric nanoparticle, more preferably a chitosan-based particle, or d) a β1,3-D-glucan particle.

The above method according to the invention is herein also defined as "MRG extraction method".

Therefore, the present method allows to obtain a fraction enriched of small RNA (sRNA) molecules.

In the context of the present invention sRNAs comprise double stranded and/or single stranded RNAs and/or single stranded RNAs with partial alignment.

In the context of the present invention "fraction" means e.g. a sample, an extract, an eluted.

In the context of the present invention the term "fungi" or "fungal" comprises the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK). The fungal cell(s) can be any fungal cell, meaning any cell present within or derived from an organism belonging to the Kingdom Fungi. The methods of the invention are applicable to all fungi and fungal cells. In one embodiment of the invention, the fungus may be a mould, or more particularly a filamentous fungus. In other embodiments of the invention, the fungus may be a yeast (e.g. Saccharomices or Pichia), or Aspergillus, Rhizopus, Neurospora. In one embodiment the fungus may be an ascomycetes fungus, i.e. a fungus belonging to the Phylum Ascomycota.

In preferred, but non-limiting, embodiments of the invention the fungus is chosen from the group consisting of edible fungi: Agaricus bisporus, and fungi of the genuses Agrocybe, Amanita, Armillaria, Artomyces, Astraeus, Aureoboletus, Auricularia, Boletus, Bovista, Butyriboletus, Calbovista, Calocybe, Calvatia, Candy Cap, Cantharellula, Cantharellus, Chalciporus, Chanterelle, Chroogomphus, Clavaria, Clavariadelphus, Clavulina, Clitocybe, Clitopilus, Coprinellus, Coprinopsis, Coprinus, Corn smut, Cortinarius, Craterellus, Cyanoboletus, Cystoderma, Cystodermella, Dacryopinax, Disciotis, Entoloma, Eritadenine, Exsudoporus, Fistulina, Floccularia, Geopora, Gliophorus, Gomphidius, Gomphus, Goossensia, Grifola, Guepinia, Gymnopus, Gyromitra, Gyroporus, Handkea, Harrya, Helvella, Hemileccinum, Hericium, Hydnum, Hygrocybe, Hygrophorus, Hypomyces, Hypsizygus, Imleria, Infundibulicybe, Laccaria, Laccocephalum, Lactarius, Lactifluus, Laetiporus, Lanmaoa, Leccinellum, Leccinum, Lentinula, Lepista, Leucopholiota, Lobaria, Lycoperdon, Mackintoshia, Marasmius, Melanoleuca, Meripilus, Morchella, Mycenastrum, Penicillium, Phallus, Phylloporus, Pleurocybella, Pleurotus, Pluteus, Polyozellus, Psathyrella, Pseudohydnum, Ramaria, Ramariopsis, Rhizopogon, Rhodocybe, Russula, Saccharomyces, Sarcodon, Sarcosphaera, Sparassis, Strobilurus, Stropharia, Suillellus, Suillus, Termitomyces, Tremella, Tricholoma, Tylopilus Verpa, Volvariella, Volvopluteus, Xerocomellus, Xerocomus, Xeromphalina.

In the context of the present invention the term "fungi" or "mushroom" are interchangeable terms.

The term "fungal cell" encompasses fungal cells of all types and at all stages of development, including specialised reproductive cells such as sexual and asexual spores. As used herein the fungal cell encompasses the fungus as such and also other life forms of the fungus, such as haustoria, conidia, mycelium, penetration peg, spore, zoospores etc.

In the context of the present invention, the term "plant" encompasses any member of the plant-kingdom according to the Linnaeus definition. Examples of plants are plants included in the genera Arabidopsis, as e.g. Arabidopsis thaliana, or Phaseolus, as e.g. Phaseolus vulgaris, or Nicotiana, as e.g. Nicotiana tabacum, or Glycine, as e.g. Glycine max, or Gossypium, as e.g. Gossypium arboreum, or Brassica, as e.g. Brassica napus, or Vitis, as e.g. Vitis vinifera, or Beta, as e.g. Beta vulgaris, or Triticum, as e.g. Triticum aestivum, or Solanum, as e.g. Solanum lycopersicum, Solanum tuberosum and Solanum melongena L., or Musa, as e.g. Musa acuminata and Musa balbisiana, or Fragaria, as e.g. Fragaria vesca, Fragaria viridis and Fragaria moschata, or Oryza, as e.g. Oryza sativa, or Hordeum, as e.g. Hordeum vulgare, or Olea, as e.g. Olea europaea, or Malus, as e.g. Malus domestica, or Allium, e.g. Alluim cepa, or Pisum, e.g. Pisum sativum, or Mentha, or Cuminum, e.g. Cuminum cyminum. The term plant also comprises lychens and algae and fruitings and any part of the plant.

The fungal or plant sample may be homogenized or fractionated, for example by grinding it into a fine powder. The expert in the art will know what is intended for fine powder.

The plant sample may comprise cotyledons, leaves (fresh or dry), sprouts, root, flowers, bulb, seed and/or fruits.

In the present invention, the fraction enriched of small RNA molecules may comprise sRNA and other RNA molecules.

The powder is mixed with a lysis buffer (LB) to release the sRNA from the fungal or plant cells.

The LB is preferably preheated at a temperature of 30-70° C., more preferably at about 55° C.

The lysis buffer may comprise a Buffer Tris HCl or any other proper buffer, having a concentration range of 10-100 mM and pH range of 7-9.5. Preferably the pH of the LB is of 8.5. The lysis buffer may comprise NaCl or any other proper chaotropic agent, in a concentration range of 100-500 mM, preferably of 0.2 M.

The lysis buffer may comprise EDTA or any other proper chelating agent, in a concentration range of 5-50 mM, preferably of 10 or 20 mM.

The lysis buffer may comprise SDS or any other proper anionic surfactants, in a concentration range of 0.5%-10%, preferably of 2%.

In another embodiement, the lysis buffer may be a 0.3M solution of sodium bicarbonate. When fresh tissue is used (grinded in Liquid nitrogen), the ratio between the weight of the powder (FW (Fresh Weight)) and LB may be in the range of 1:1 to 1:5. In the case of lyophilized tissue (which is then grinded), the ratio between DW (Dry Weight) and LB may be in the range of 1:5 to 1:25.

The incubation with LB may be carried out at a temperature of 20-60° C., preferably at RT. The incubation is preferably carried out by mixing. The incubation is preferably carried out for 5-15 minutes, more preferably 10 minutes.

After incubation with LB, the liquid phase my be separated and the solid phase discarded. An activated charcoal may be added to the resulting liquid phase. Preferably, the activated charcoal is at a concentration of 10-20 mg/ml, more preferably 30 mg/ml. The solution may then be mixed for 5-15 minutes, preferably 10 minutes. The charcoal and other particulate are then removed e.g. by filtration.

An alcohol solution is added to, mixed with, or incubated with the solution in embodiments of the invention. An alcohol solution comprises at least one alcohol. The alcohol solution can be about, be at least about, or be at most about 5,10, 15, 20,25, 30,35, 40,45, 50, 55,60, 65,70, 75,80, 85,90, 95, or 100% alcohol, or any range therein. In certain embodiments, it is added to a powder to make the final solution have a concentration of alcohol of about, about at least, or about at most 5, 6,7, 8,9, 10,11, 12,13, 14,15, 16,17, 18,19, 20,21, 22,23, 24,25, 26,27, 28,29, 30,31, 32,33, 34,35, 36,37, 38,39, 40,41, 42,43, 44,45, 46,47, 48,49, 50, 51, 52,53, 54,55, 56,57, 58,59, 60,61, 62,63, 64,65, 66,67, 68,69, 70,71, 72,73, 74,75, 76,77, 78,79, 80,81, 82, 83, 84,85, 86,87, 88,89, or 90%, or any range therein. In specific embodiments, the amount of alcohol solution added to the powder gives it an alcohol concentration of 60%. Alcohols include, but are not limited to, ethanol, propanol, isopropanol, and methanol, with isopropanol as preferred. An alcohol solution may be also used in additional steps of methods of the invention to precipitate RNA.

Isopropanol is preferably added at a concentration of 100%.

Purification of small RNAs from the solution includes using a solid support, such as a mineral or polymer support.

Essential according to the invention is the use of a nucleic acid (NA) binding solid support e.g. silica particles capable of binding the NA in the presence of a chaotropic substance. By silica are meant SiO2 crystals and other forms of silicon oxide, such skeletons of diatoms built up from SiO2, amorphous silicon oxide and glass powder. Also alkylsilica, aluminum silicate (zeolite), activated silica with —NH2, latex particles, certain polymeric materials forming the inside wall of a cuvette or a microtiter plate, or filter materials for example consisting of nitrocellulose are suitable as nucleic acid binding solid phase according to the invention.

A "solid support" or "support" refers to a physical structure containing a material which contacts the solution and that does not irreversibly react to macromolecules in the solution, particularly with small RNA molecules. In particular embodiments, the solid support binds small RNA molecules; in additional cases, it binds small RNA molecules, but does not bind one or more other types of macromolecules in the sample. The material in the solid support may include a mineral or polymer, in which case the support is referred to as a "mineral or polymer support." Mineral or polymer supports include supports involving silica. Supports include, but are not limited to, beads, columns and filters. In further embodiments, the mineral or polymer support is a silica filter or column.

In a preferred embodiment, magnetic silica beads are added to the solution, preferably at a concentration of 1-5 mg/mL, more preferably at a concentration of 2.5 mg/mL.

In a more preferred embodiment, the magnetic silica beads are basic magprep silica [Merck Millipore], having a diameter of about 1 μm, a composition of >95% magnetite, a surface area of 16-22 m2/mg, a binding capacity of >10 μg DNA or RNA per mg.

The incubation with silica beads preferably lasts 10 minutes and is carried out by gentle shaking.

The magnetic beads are then preferably captured with magnete and the liquid is diascarded.

In an alternative embodiment, the solution is poured through a filter, preferably a muslin filter, into a Perspex column comprising silica gel, preferably at a concentration of 1.5 g/gDW tissue.

In particular, amorphous silica Sigma 274739 (50-70 mesh) was resuspended with 10% HCl, and allowed to settle for 24 h. The supernatant was aspirated and discarded. The pellet was resuspended with 6 ml of 0.1 M HCl and then aliquoted and stored at 4 C.

In a preferred embodiment, after addition of isopropanol, the liquid phase is pured into a column containing 1-5 μm diameter silicon dioxide beads, preferably 5 mg/g tissue. In an alternative embodiment, 1-5 μm diameter silicon dioxide beads, preferably 100 mg/g tissue are added after the addition of isopropanol and preferably agitated for 5-15 minutes, preferably for 10 minutes.

The liquid phase may then be removed.

Alternatively, in some embodiments, the mineral or polymer support may include polymers or nonpolymers with electronegative groups. In some embodiments, the material is or has polyacrylate, polystyrene, latex, polyacrylonitrile, polyvinylchloride, methacrylate, and/or methyl methacrylate.

After a solution is applied or mixed with a solid support, the material may be washed with a solution. In some embodiments, a mineral or polymer support is washed with a first wash solution comprising alcohol, after applying the lysate to the mineral or polymer support. The methods of the invention may involve 1,2, 3,4, 5 or more washes with the wash solution. The wash solution used when more than one washing is involved may be the same or different. It is generally understood that molecules that come through the material in a wash cycle are discarded.

In a preferred embodiment, beads or columns are washed three times with a 80% or 85% solution of ethanol.

In an alternative embodiment, the column is washed with 10 volumes of a 80% solution of ethanol.

Beads or column are then preferably dried to remove residual ethanol.

In other methods of the invention, the desired RNA molecules are eluted from the solid support. In certain embodiments, small RNA molecules are eluted from a solid support such as a mineral or polymer support at a temperature of about 60° C. to about 100° C. It is contemplated that the temperature at which the RNA molecules are eluted is about or at least about 5,10, 15, 20,25, 30,35, 40,45, 50,55, 60,65, 70,75, 80,85, 90,95, 100° C. or more, or any range therein.

The molecules may be eluted with any elution solution. In some embodiments, the elution solution is an ionic solution, that is, it includes ions. In particular embodiments, the elution solution includes up to 10 mM salt. It is contemplated to be about, at least about, or at most about 0.1, 0.5, 1,2, 3,4, 5,6, 7,8, 9,10 or more mM salt. In certain embodiments, the salt consists of a combination of Li+, Na+, K+, or NH4+as cation and Cl−, Br, I−, ethylenediaminetetraacetate, or citrate as anion.

In a preferred embodiment of the method of the invention, the sRNA are eluted with RNAse free water, more preferably at a temperature of 65° C. Volume range for the water for the beads is 60-200 uL/mg beads (0.6-2:1 v/W). For the silica gel the volume range is 1-5 mL/g resin (1-5:1 v/W). In a preferred embodiment, water is used at a concentration of 1 Volume or of 125 μL/mg of beads.

The present method may be used also for isolating small RNA from plants.

The present invention also concerns kits for isolating small RNA molecule (or fractions enriched of small RNA molecules), such as miRNA and/or siRNA from a fungi or plant sample, particularly a cell or tissue sample. Thus, any of the compositions discussed above can be included with any other composition discussed above for inclusion in a kit. In some embodiments, there are kits for isolating small RNA molecules comprising: a) isopropanol, b) one or more small RNA wash solution (s), and e) an elution solution.

In preferred embodiment, the kit contains: a) lysis buffer; b) isopropanol ; c) a wash solution comprising 80% ethanol; f) an elution solution comprising RNA-se free water; g) a gel loading buffer II ; h) collection tubes; and i) filter cartridges.

In some embodiments, kits of the invention include one or more of the following in a suitable container means (consistent with compositions discussed above): a silica filter or column; elution buffer; wash buffer; alcohol solution; and RNase inhibitor.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (they may be packaged together), the kit also will generally contain a second, third or other additional container into which the additional components may be separately placed. However, various combinations of components may be comprised in a vial. The kits of the present invention also will typically include a means for containing the RNA, and any other reagent containers in close confinement for commercial sale. Such containers may include injection or blow-molded plastic containers into which the desired vials are retained. When the components of the kit are provided in one and/or more liquid solutions, the liquid solution is an aqueous solution, with a sterile aqueous solution being particularly preferred.

However, the components of the kit may be provided as dried powder (s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the RNA or that protect against its degradation. Such components may be RNAse-free or protect against RNAses. Such kits generally will comprise, in suitable means, distinct containers for each individual reagent or solution.

The sRNA molecules obtained by the present method may be used in the food or nutraceutical field. Food products or foodstuffs that may include said sRNA molecules are for example beverages, for instance sport drinks, fruiting juices, and alcoholic drinks as well as liquid preparation to be added to drinking water and liquid food. In another embodiment food products or foodstuffs comprise solid or semi-solid foods, e.g. baked goods, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour). The term food products or foodstuffs also includes functional foods and prepared food products, the latter referring to any pre-packaged food approved for human consumption.

The resulting food products or foodstuffs contain an enlarged amount and/or concentration of plant or fungal sRNA molecules compared to the food products or foodstuffs without addition of such food additive.

In a preferred embodiment, such food products or foodstuffs contain an amount of plant or fungal sRNA or sRNA molecules which is at least 10% higher than the amount in the food product or foodstuff without addition of such food additive comprising a sRNA molecules, more preferably the amount is at least 20%, 50%, 100% or 200% higher than in the food product or foodstuff without addition of such food additive.

Food compositions and dietary supplements are preferably administered orally. Dietary supplements may be delivered in any suitable format, preferably for oral delivery. The ingredients of the dietary supplement of this invention are acceptable excipients and/or carriers for oral consumption. The carrier may be a liquid, gel, gelcap, capsule, powder, solid tablet (coated or non-coated), tea, or the like.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food, or by otherwise adding to a food e.g. enclosed in caps of food or beverage container for release immediately before consumption.

The dosage of composition comprising sRNA molecules of the invention as food additive vary depending upon known factors, such as its mode and route of administration; the age, health and weight of the recipient; the nature and extent of the symptoms; the kind of concurrent treatment; the frequency of treatment; and the effect desired which can be determined by the expert in the field with normal trials. Typically, dosage amounts of the plant or fungal sRNA molecules may vary from 10-20 mg sRNA molecules per application to 1-2 mg sRNA molecules for daily use/application.

The dietary supplement may be administered as single dose or multiple doses.

Suitable routes of administration of the pharmaceutical composition of the invention include, for example, oral, intranasal and parenteral administration.

The pharmaceutical composition of the present invention can be administered in the form of a dosage unit, for example tablets or capsules, or a solution.

Suitable pharmaceutical carriers are e.g. described in Remington's Pharmaceutical Sciences, a standard reference text in this field. The pharmaceutical composition may further comprise conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The pharmaceutical compositions may be administered as single dose or multiple doses.

The compositions according to the present invention may be in any galenic form that is suitable for administering to the animal body including the human body, more in particular in any form that is conventional for oral administration, e.g. in solid form, for example tablets, pills, granules, dragees, capsules, and effervescent formulations such as powders and tablets, or in liquid form, for instance in the form of solutions, emulsions or suspensions, for example as pastes and oily suspensions. The pastes may be filled into hard or soft shell capsules, whereby the capsules feature e.g. a matrix of (fish, swine, poultry, cow) gelatin, plant proteins or lignin sulfonate. Examples for other application forms are forms for transdermal, parenteral, topical or injectable administration. The pharmaceutical compositions may be in the form of controlled (delayed) release formulations. Topical formulation may contain e.g. ointments, creams, gels, lotions, solutions. In the present invention the term "effective amount" shall mean an amount which achieves a desired effect or therapeutic effect as such effect is understood by those of ordinary skill in the art. For injection, including, without limitation, intravenous, intramuscular and subcutaneous injection, the compounds of the invention may be formulated in aqueous solutions, preferably in physiologically compatible buffers such as physiological saline buffer or polar solvents including, without limitation, a pyrrolidone or dimethylsulfoxide.

Formulations for injection may be presented in unit dosage form, e.g. in ampoules or in multi-dose containers. Pharmaceutical compositions for parenteral administration include aqueous solutions of a water soluble form, such as, without limitation, a salt of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxym ethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl- methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

For administration by inhalation, the sRNA molecules of the present invention can conveniently be delivered in the form of an aerosol spray using a pressurized pack or a nebulizer and a suitable propellant. The sRNA molecules may also be formulated in rectal compositions such as suppositories or retention enemas, using, e.g., conventional suppository bases such as cocoa butter or other glycerides.

In addition to the formulations described previously, the sRNA molecules may also be formulated as depot preparations. Such long acting formulations may be administered by implantation (for example, subcutaneously or intramuscularly) or by intramuscular injection. The compounds of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Determination of a therapeutically effective amount is well within the capability of those skilled in the art, especially in light of the disclosure herein.

The administration of such sRNA molecules may occur through complexing of the sequence with a suitable delivery system such as complexation with cationic liposomes or inclusion in nanovesicles. The delivery system can then be formulated for oral (including sub-lingual) administration as dietary supplement or directly integrated in food matrix or drinks for regular use. The daily doses may be in the range of 1-5 mg of active principle.

The delivery system may be formulated for topical administration. The daily doses may be in the range of 1-5 mg of active principle.

The delivery system may be formulated for intravenous administration with dosage over 10 mg of active principle.

The above defined sRNAs of 15-60 bp of length extracted from plants or mushrooms may be functionalized to enhance their bioavailability and anti-inflammatory efficacy When dietary vegetables are consumed through the diet a small fraction of the microRNAs originally present in the food matrix passes through the CI tract and becomes available in the bloodstream (0.05%-0.5%).

Such reduced bioavailability limits the anti-inflammatory efficacy towards human cells and organs of miRNAs and sRNAs naturally absorbed through the diet.

Moreover, bioavailable dietary naked miRNAs or sRNAs may be subjected to degradation or structural modification within the bloodstream with ensuing loss of bioactivity.

Inventors have discovered that complexation of 15-60 bp sRNAs extracted from plants or mushrooms with liposomes, exosomes or nanoparticles enables their effective uptake by dendritic cells of the human immune system.

Moreover complexation of such bioactive compounds will preserve integrity and reduce degradation in case of :
  oral consumption: during the mastication and passage through the GI tract.
  topic application: during application on skin surface and permeation in the dermis
  intravenous application: for movement within the bloodstream and transfer to recipient cells and organs In case of oral consumption or topic application, complexation will also facilitate their transfer into the bloodstream.

Complexation with cationic liposomes occurs naturally by physico-chemical interaction sRNAs are negatively charged in solution.

In a preferred embodiment the sRNAs as described above are provided within a delivery vehicle, optionally wherein the delivery vehicle is selected from liposomes, particularly cationic liposomes, liposome comprising lipids, or nanovesicles. Many methods are available for preparing liposomes, as described in, for example, Szoka et al., Ann. Rev. Biophys. Bioeng., 9:467 (1980) and U.S. Pat. Nos. 4,235,871, 4,501,728, 4,837,028, and 5,019,369.

In an embodiment of the invention, at least part of the lipids of the liposomes are selected from the group consisting of phospholipids, sterols and sterol derivatives.

In a particular embodiment of the invention wherein the lipid of the liposomes comprises or constitutes a member selected from the group consisting of phosphatidylcholine (PC), phosphatidylethanolamine (PE), phosphatidylserine (PS), phosphatidylglycerol (PG), phosphatidylinositol (PI), phosphatidic acid (PA), DPG (bisphosphatidyl glycerol), PEOH (phosphatidyl alcohol), cholesterol, ergosterol and lanosterol.

In a further embodiment, the liposome comprises phosphatidylcholines selected from the group consisting of 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2 -palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine.

In an embodiment of the inventions the liposome comprises phosphatidylethanolamines selected from the group consisting of 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl -2-palmitoyl-phosphatidylethanolamine, 1-oleoyl -2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; the phosphatidylserines are selected from the group consisting 1,2-dioleoyl-phosphatidylserine, 1,2-dipalmitoyl -phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl -2-oleoyl-phosphatidylserine and 1-stearoyl-2-oleoyl-phosphatidylserine; the phosphatidylglycerols are selected from the group consisting 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl -2-stearoyl -phosphatidylglycerol, 1-palmitoyl-2-oleoyl-phosphatidylglycerol and 1-stearoyl-2-oleoyl-phosphatidylglycerol; the phosphatidic acids are selected from the group consisting of di-palmitoyl-glycerophosphatidic acid, di-stearoyl-glycerophosphatidic acid, di-myrostoyl-glycerophosphatidic acid, di-oleoyl-glycerophosphatidic acid, palmitoyl-oleoyl-glycerophosphatidic acid.

In nnother embodiment of the liposome of the invention, the lipid comprises or constitutes phosphatidylglycerol (PG), phosphatidylethanolamine (PE), phosphatidylserine (PS), phosphatidylcholine (PC), phosphatidylinositol (PI), phosphatidic acid (PA), DPG (bisphosphatidyl glycerol), PEOH (phosphatidyl alcohol),cholesterol, phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl -2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl -phosphatidylethanolamine, 1-oleoyl-2-palmitoyl-phosphatidylethanolamine, 1-oleoyl -2-stearoyl -phosphatidylethanolamine, 1-palmitoyl -2-oleoyl-phosphatidylethanolamine, 1-stearoyl-2 -oleoyl -phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl -2-oleoyl-phosphatidylserine and 1-stearoyl-2-oleoyl-phosphatidylserine; phosphatidylglycerols such as 1,2-dioleoyl -phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl -2-oleoyl-phosphatidylglycerol and 1-stearoyl-2-oleoyl-phosphatidylglycerol; 1,2-dioctadecanoyl- sn-glycero-3 -ethylphosphocholine (Ethyl PC); pegylated lipids; pegylated phospoholipids such as phophatidylethanolamine-N- [methoxy(polyethyleneglycol)-1000], phophatidylethanolamine-N-[methoxy (polyethyleneglycol)-2000], phophatidylethanolamine-N-[methoxy(polyethylene glycol)-3000], phophatidylethanolamine-N-[methoxy (polyethyleneglycol)-5000]; pegylated ceramides such as N-octanoyl-sphingosine-1-{succinyl[methoxy(polyethyleneglycol)1000]}, N-octanoyl-sphingosine -1-{succinyl [methoxy(polyethylene glycol)2000]}, N-octanoyl-sphingosine- 1-{succinyl [methoxy(polyethyleneglycol)3000]}, N-octanoyl-sphingosine-1-{succinyl [methoxy(polyethyleneglycol)5000]}; lyso-phosphatidylcholines, lyso-phosphatidylethanolamines, lyso-phosphatidylglycerols, lyso-phosphatidylserines, ceramides; sphingolipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl -2-succinylglycerol; 1-alkyl-2-acyl-phosphatidylcholines such as 1-hexadecyl-2-palmitoyl -phosphatidylcholine; 1-alkyl-2-acyl-phosphatidylethanolamines such as 1-hexadecyl-2-palmitoyl -phosphatidylethanolamine; 1-alkyl-2-acyl-phosphatidylserines such as 1-hexadecyl-2-palmitoyl -phosphatidylserine; 1-alkyl-2- acyl-phosphatidylglycerols such as 1-hexadecyl-2-palmitoyl -phosphatidylglycerol; 1-alkyl-2-alkyl-phosphatidylcholines such as 1-hexadecyl-2-hexadecyl -phosphatidylcholine; 1-alkyl-2-alkyl-phosphatidylethanolamines such as 1-hexadecyl-2-hexadecyl -phosphatidylethanolamine; 1-alkyl-2-alkyl-phosphatidylserines such as 1-hexadecyl-2-hexadecyl -phosphatidylserine; 1-alkyl-2-alkyl-phosphatidylglycerols such as 1-hexadecyl-2-hexadecyl -phosphatidylglycerol; and N-Succinyl-dioctadecylamine; palmitoylhomocysteine.

An embodiment of the invention is a liposome, wherein at least part of the lipids is a cationic lipid.

An embodiment of the invention is a liposome, wherein the cationic lipids are selected from the group consisting of stearylamine (SA), lauryltrimethylammonium bromide; cetyltrimethyl-ammonium bromide, myristyl trimethylammonium bromide, dimethyldioctadecylammonium bromide (DDAB), 3β-[N-(N',N'-dimethylaminoethane)- carbamoyl] cholesterol (DC-Cholesterol), 1,2- ditetradecanoyl-3-trimethylammonium-propane (DMTAP), 1,2-dioctadecanoyl-3-trimethylammonium -propane (DOTAP) and DOTAP derivatives such as 1,2-di-(9Z-octadecenoyl)-3-trimethylammonium-propane and 1,2-dihexadecanoyl-3-trimethylammonium-propane, 1,2-di-(9Z-octadecenoyl) -3-dimethylammonium-propane (DODAP) and DODAP derivatives such as 1,2-ditetradecanoyl -3-dimethylammonium-propane, 1,2-dihexadecanoyl-3-dimethylammonium-propane, and 1,2-dioctadecanoyl-3-dimethylammonium-propane, 1,2-di-O-octadecenyl-3-trimethylammonium propane (DOTMA), 1,2-dioleoyl-c-(4'-trimethylammonium)-butanoyl-sn-glycerol (DOTB), dioctadecylamide-glycylspermine, SAINT-2, polycationic lipid 2,3-dioleyloxy-N-[2 (spermine-carboxamido)ethyl]-N,N-dimethyl-1-propanaminiumtrifluoroacetate (DOSPA), and GL67TM.

A particular embodiment of the invention is a liposome, wherein the cationic lipids are selected from the group consisting of stearylamine (SA), 1,2-dioctadecanoyl-3-trimethylammonium-propane (DOTAP) and 1,2-di-(9Z-octadecenoyl)-3-dimethylammonium-propane (DODAP), preferably 1,2-dioctadecanoyl -3-trimethylammonium-propane (DOTAP).

Preferred cationic lipids are DOTAP and DOTAP derivatives. Additional examples of cationic lipids and lipid components may be found in or made according to U.S. Pat. No. 4,804,539.

An embodiment of the invention is a liposome, wherein at least part of the lipids is a cationic lipopeptide selected from the group consisting of a lipid polyarginine conjugate, a lipid TAT conjugate, a lipid polylysine conjugate, or a cationic liposaccharide or lipopolysaccharide such as a lipid chitosan conjugate.

In a preferred embodiment, the lipids are capable of forming a liposome. In particular, cationic lipids are suitable for this purpose.

Cationic lipids preferably include DOTAP, DOPE, DC-Chol/DOPE, DOTMA, and DOTMA/DOPE.

Cationic Lipids: Cationic lipids carry a net positive charge at about physiological pH. Suitable cationic lipids include, but are not limited to, N,N-dioleyl-N,N-dimethylammonium chloride ("DODAC"); N-(2,3-dioleyloxy)propyl-N,N-N-triethylammonium chloride ("DOTMA"); N,N-distearyl -N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N-(N',N'-dimethylaminoethane)-carbamoyl)cholesterol ("DC-Chol"), N-(1-(2, 3-dioleyloxyl)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl -2,3-dioleyloxy)propylamine ("DODMA"), and N-(1,2-dimyristyloxyprop-3-yl)-N,N-dimethyl -N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

Additional cationic lipids include 1,2-dilinoleyloxy-3-dimethylaminopropane (DLinDMA) 1,2-Dilinoleoyl -3-dimethylaminopropane (DLinDAP), 1-Linoleoyl-2- linoeyloxy-3-dimethylaminopropane (DLin-2-DMAP), 1,2-Dilinoleylcarbamoyloxy-3-dimethylaminopropane (DLin-C-DAP), 1,2-Dilinoleylthio-3-dimethylaminopropane (DLin-S-DMA), 2,2-Dilinoleyl-4-dimethylaminomethyl -[1,3]-dioxolane (DLin-K-DMA).

An embodiment of the invention is a liposome or a vescicle, with a particle size of between 0.1 and 100 um In certain embodiments, the ratio of total lipid to sRNA is from 5 to 35 (i.e. from 5 to 1 to 35 to 1, lipid weight to sRNA weight). In certain embodiments, the ratio of total lipid to sRNA is from 5 to 15 (i.e. from 5 to 1 to 15 to 1, lipid weight to sRNA weight).

In a yet further preferred embodiment, exosomes may be used. Such exosomes and their preparation are described e.g. in Montecalvo et al. (2012, Blood, 119: 756-766, and Stoorvogel, 2012, Blood, 119: 646-648). For example, exosomes loaded with plant or fungal sRNA or sRNA extract(s) or compositions comprising 2 or more plant or fungal sRNA or sRNA extract(s) may be used. For example, exosomes loaded with plant miRNA may be used.

Polymeric nanoparticles formed by self-assembly of polycations with siRNA can be used for extracellular delivery, cellular uptake and intracellular trafficking as a strategy to improve the therapeutic potential of siRNA. Polycationic polymer-based nanoparticle (or polyplex) systems used for site-specific delivery, cellular uptake and intracellular trafficking of siRNA. Such nanoparticles and in particular chitosan-based particles and their preparations are described e.g. in Østergaard et al., Therapeutic Applications of RNAi: Methods and Protocols, Humana Press 2009.

For example, nanoparticles loaded with plant or fungal sRNA or sRNA extract(s) or compositions comprising 2 or more plant or fungal sRNA or sRNA extract(s) may be used.

Another delivery strategy is via β1,3-D-glucan particles (GP), hollow and porous microspheres derived from Saccharomyces cerevisiae (Baker's yeast) that provide an efficient system for encapsulation, protection, and oral or systemic macrophage-targeted delivery of macromolecules, such as DNA, siRNA and proteins using either a polyplex or layer-by-layer (LbL) synthesis methods. Such particles and their preparations are described e.g. in Soto and Ostroff, Nanomaterials for Biomedicine, 3, 57-79 2012. In a particular embodiement, plant or fungal sRNA is encapsulated in 2-4 μm hollow β1,3-D- glucan particles.

For example glucan particles loaded with plant or fungal sRNA molecules of the invention may be used.

The "MRG extraction method" allows selective extraction and purification of low molecular weight ribonucleic acid species (sRNAs) from plants and/or mushroom-derived biomass which display anti-inflammatory properties (*Plant microRNAs as novel immunomodulatory reagents. Scientific Reports* 2016 Cavalieri et al.). Unlike other existing methods, which have all been designed for analytical purposes, the MRG protocol aims at the production of sRNA extracts for the food industry and does not involve the use of solvents or toxic reagents and achieve the selective extraction of sRNA from extracts through ionic interaction with activated silica gel. It is important to note that the MRG method aims at the selective enrichment in the extracts of the microRNA and siRNA fraction which comprise small RNA of length between 19 and 24 nt. These species are present both in the single stranded and double stranded configurations (ssRNAs and dsRNAs) and are characterized by the presence of a phosphate group at the 5' ends and a methyl group at the 3' ends. These properties make these molecular species (particularly the double stranded configurations) much more resistant than other sRNAs to degradation during extraction.

The present invention will be illustrated by means of non limiting examples in reference to the following figures.

FIG. 1. A method for lab-scale purification of sRNA from fungi.

Figure 2:
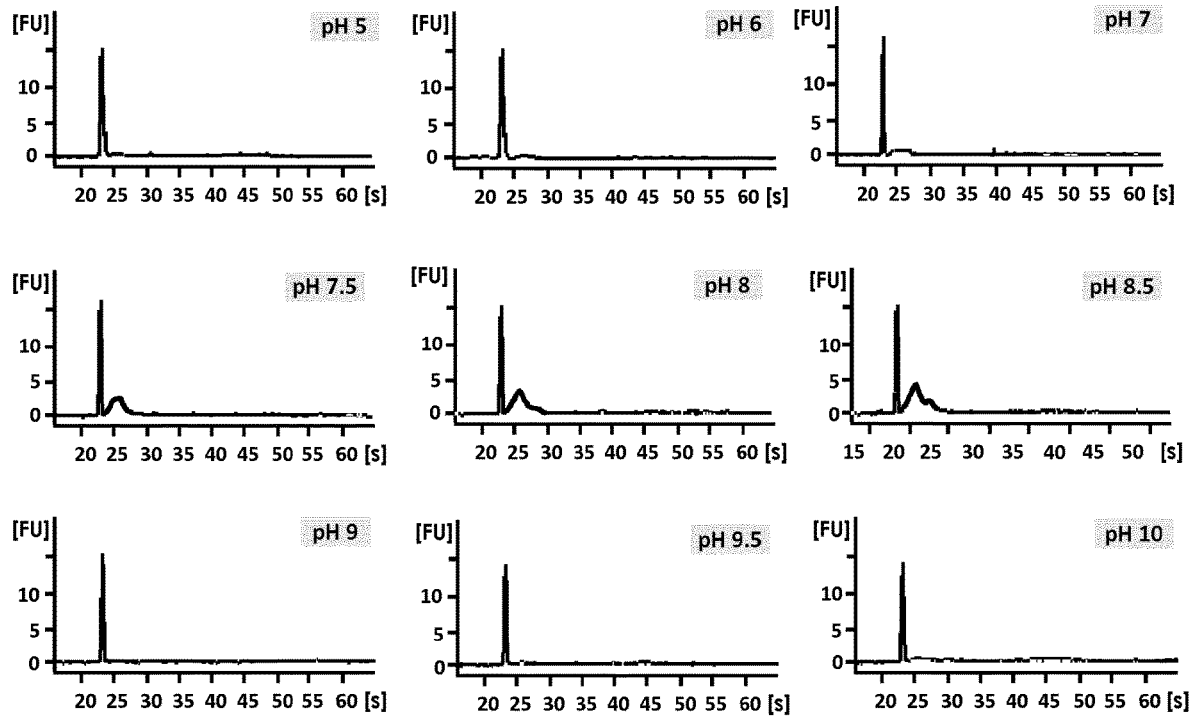

FIG. 2. Electropherograms of sRNA extracts obtained using LB with different pH.

Figure 3:
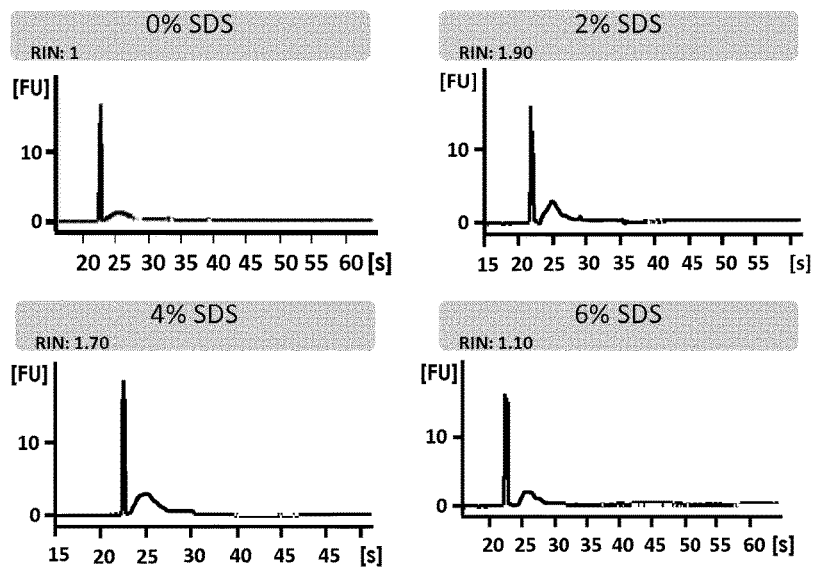

FIG. 3. Electropherograms of sRNA extracts obtained using different SDS concentrations in the LB.

Figure 4:
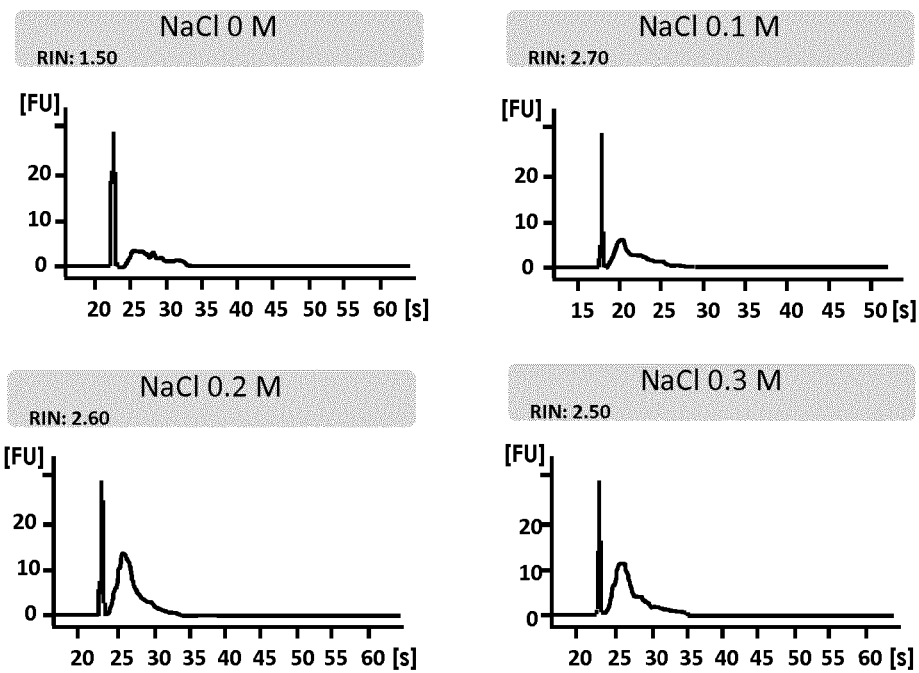
Figure 5:
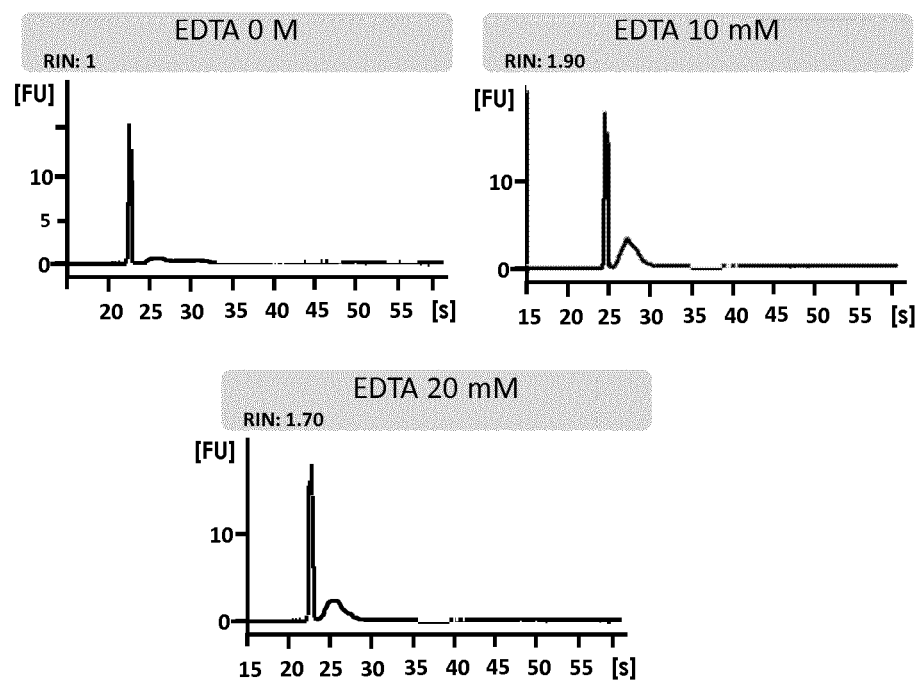

FIG. 4. Electropherograms of sRNA extracts obtained using different NaCl concentrations in the LB FIG. 5. Electropherograms of sRNA extracts obtained using different EDTA concentrations in the LB.

Figure 6:
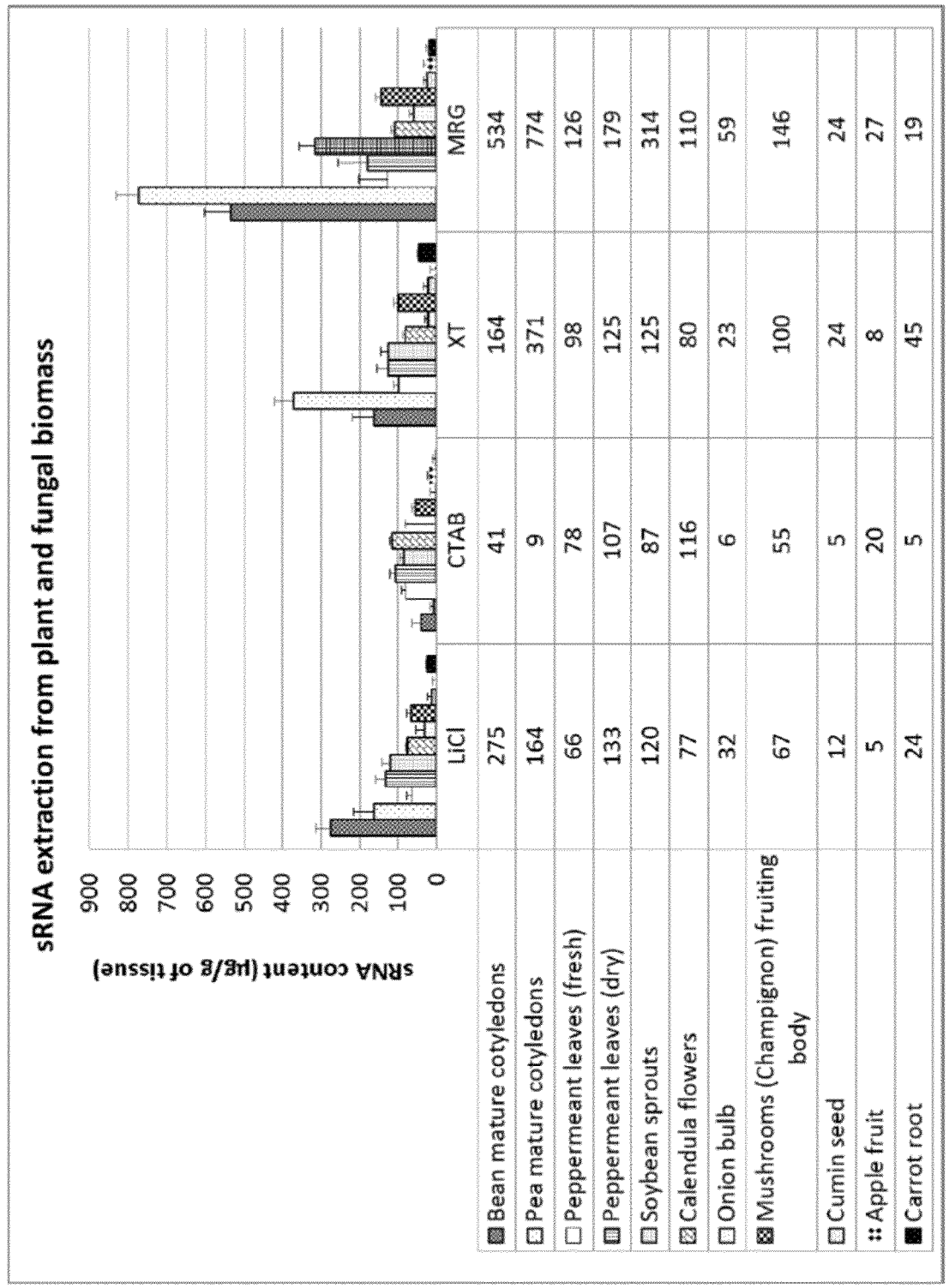

FIG. 6. Total sRNA extracted from various plants and fungal tissues (100 mg) using the "MRG sRNA extraction method". The total sRNA content of the DW eluate from the silicon dioxide beads was determined using the Agilent RNA 6000 Nano Kit through the Bioanalyzer instrument /Agilent Technologies) and data are expressed as ug/g of tissue±S. D.

Figure 7:
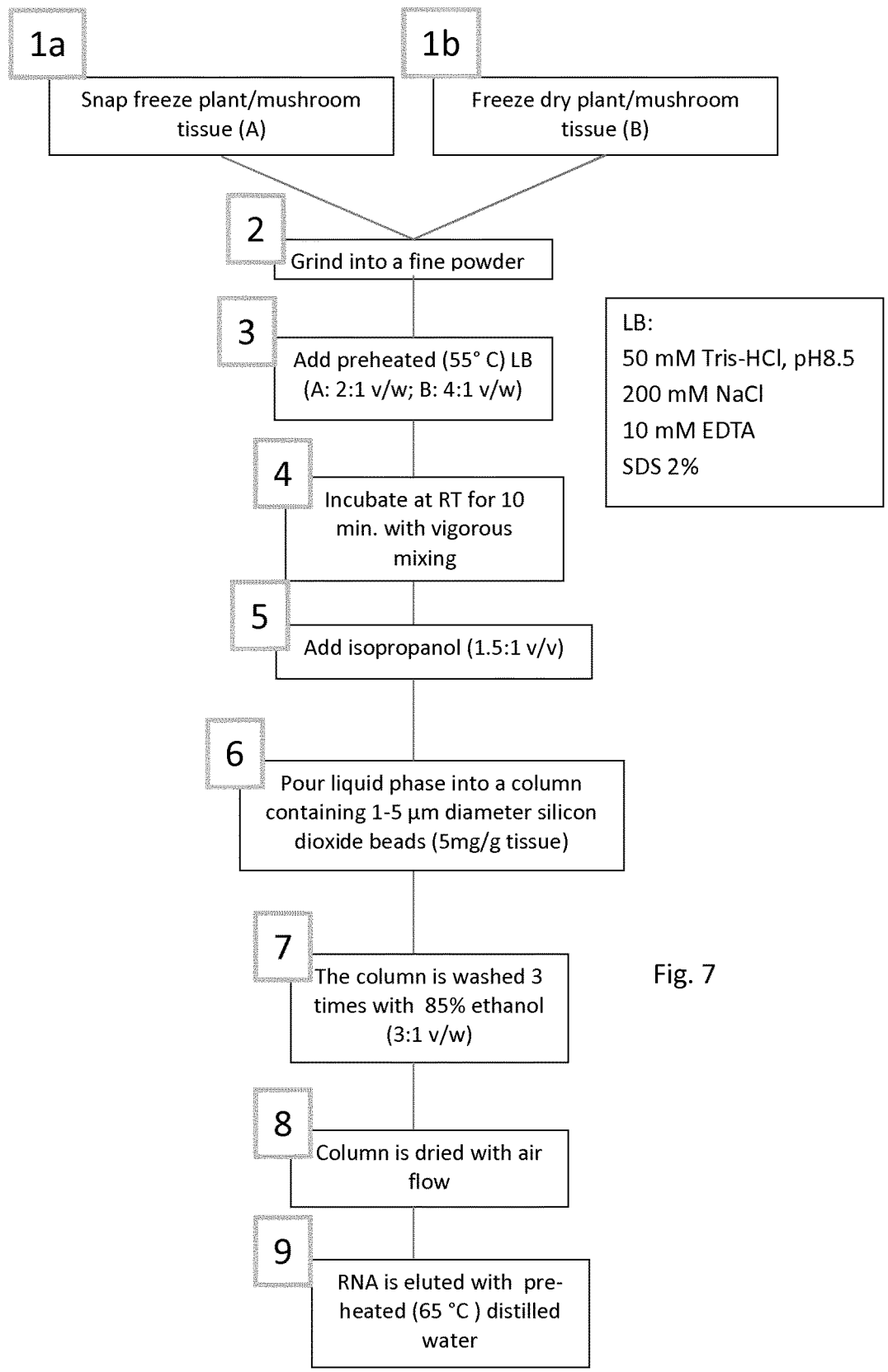

FIG. 7. MRG sRNA extraction method (column) from plant or fungi

Figure 8:
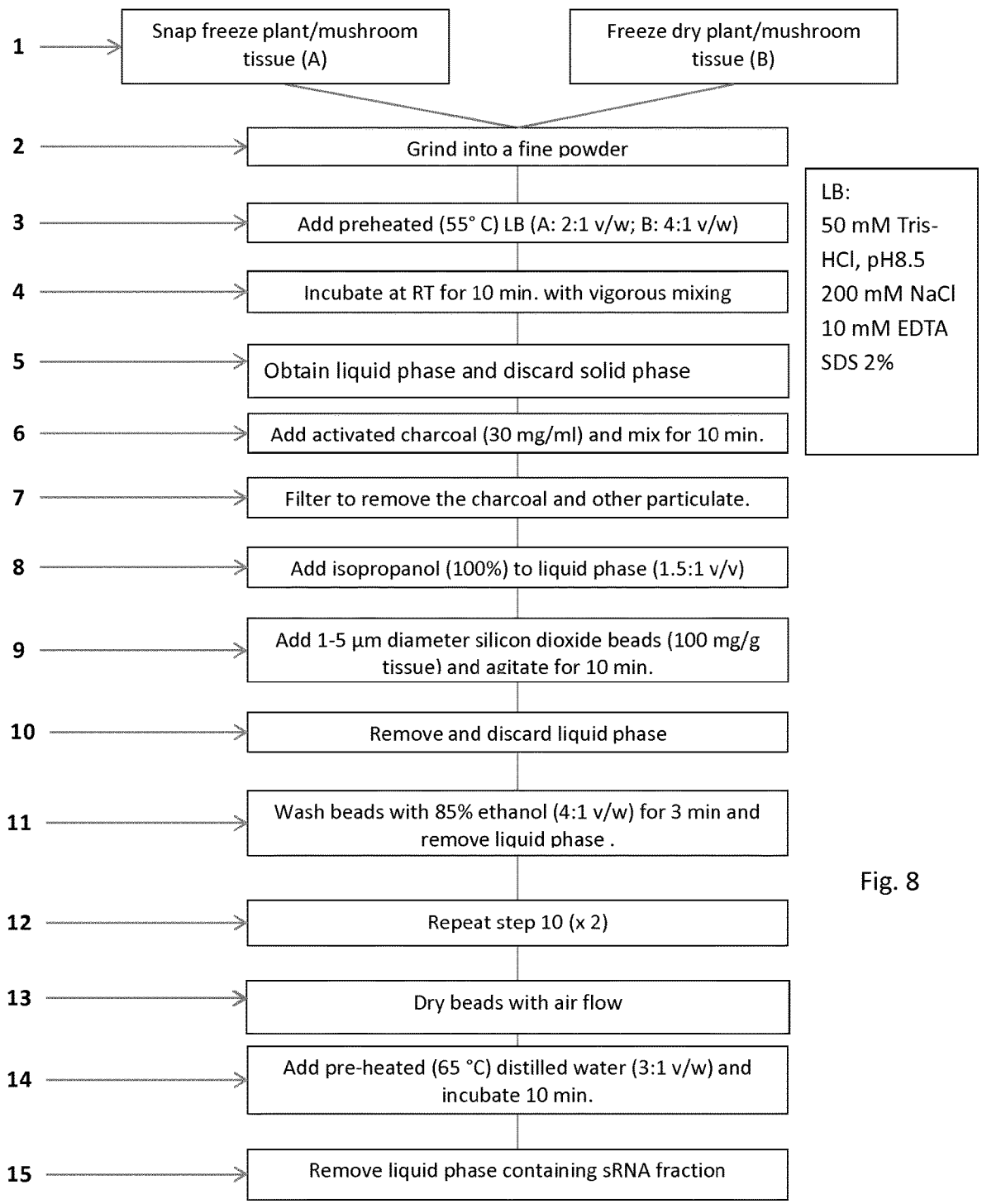

FIG. 8. MRG sRNA extraction method (no column) from plant or fungi

Figure 9:
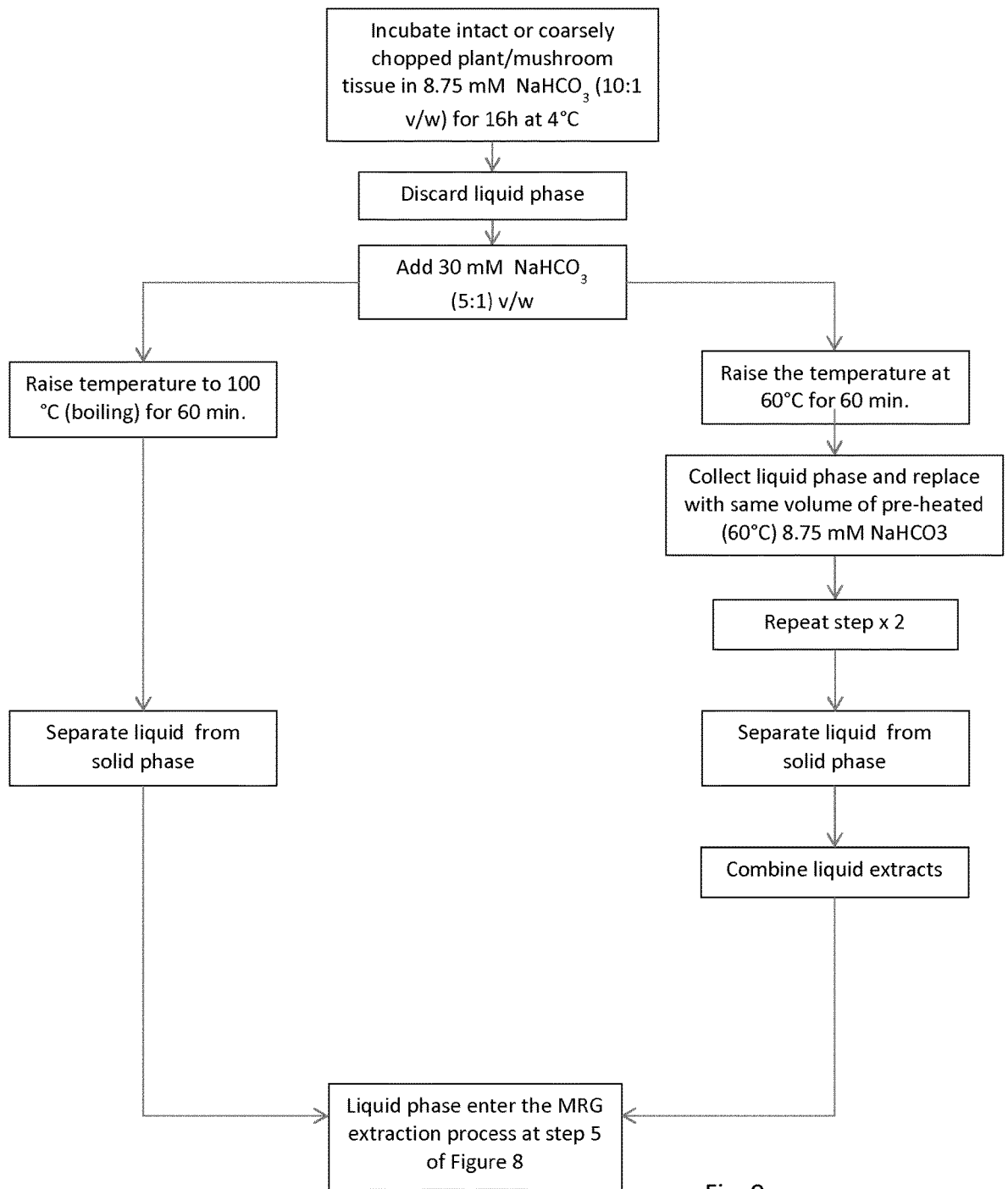

FIG. 9. Exctraction in diluted bicarbonate solution

Figure 10:
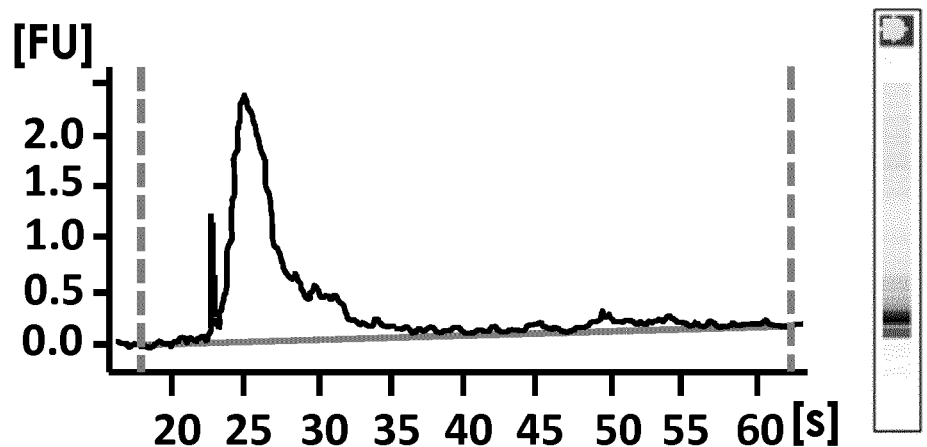
Figure 10:
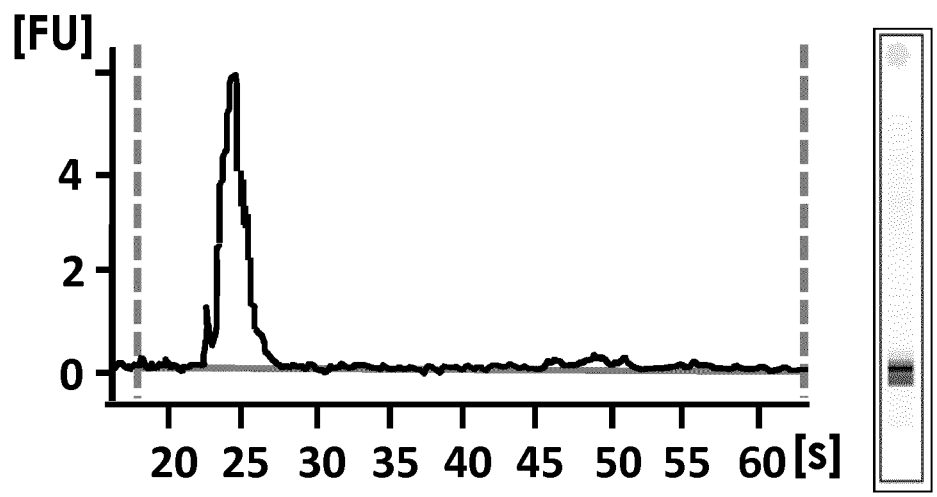

FIG. 10. The figure shows the RNA profile of concentrated sRNA extracts before (A) and after (B) RNAse A treatment using the Agilent RNA 6000 Nano Kit through the Bioanalyzer instrument (Agilent Technologies).

Figure 11:
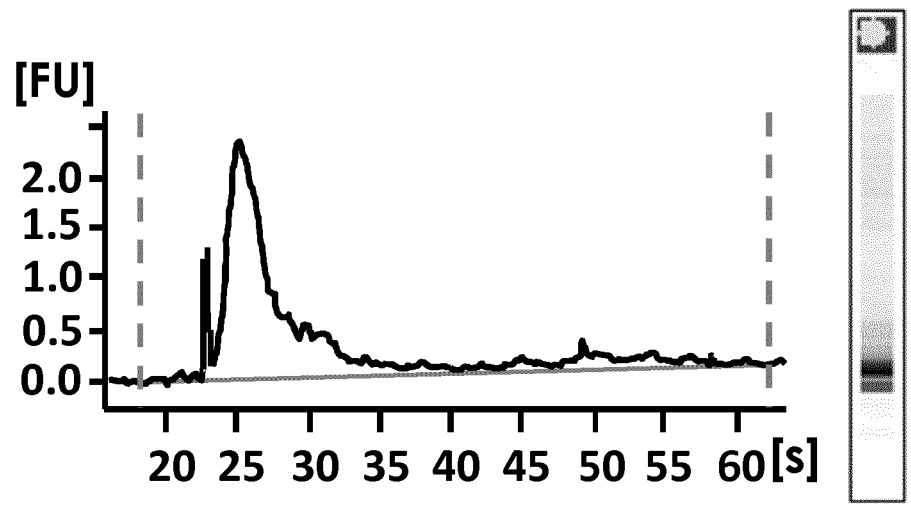
Figure 11:
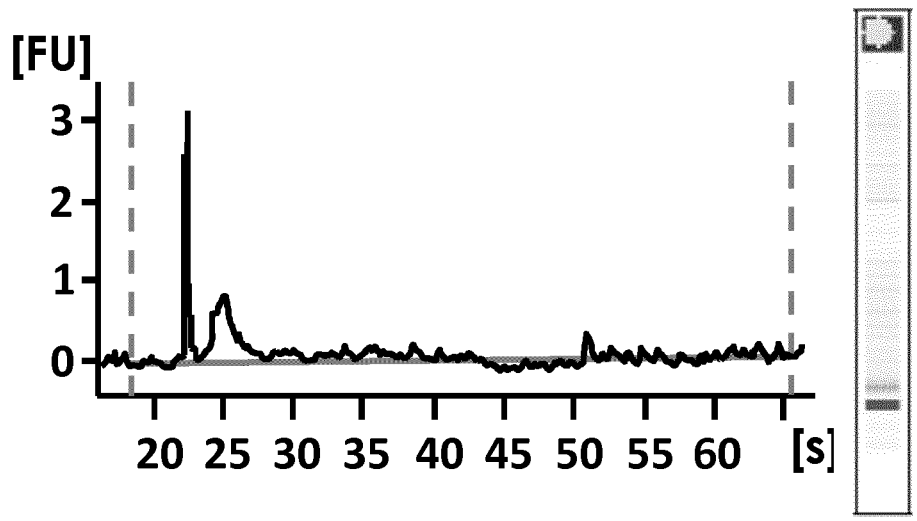

FIG. 11. The figure shows the RNA profile of concentrated sRNA extracts before (A) and after (B) p 19siRNA binding protein treatment using the Agilent RNA 6000 Nano Kit through the Bioanalyzer instrument (Agilent Technologies)

EXAMPLES

Materials and Method

Starting protocol for the extraction of sRNA from mushroom tissue based on the utilization of non-toxic reagents for tissue lysis and magnetic silica beads for the isolation of sRNA from the extraction solution.

Basic extraction protocol (BEP):
1. Extraction of sRNA: 100mg of mushroom tissue (fruit body of Agaricus bisporus) is incubated with 200 μL of pre-heated (55° C.) lysis buffer (LB) at room T for 10 min. with vortexing (30 sec. every 2 min).
2. Binding of sRNA to magnetic beads: after centrifugation, the extract (200 μL) is transferred to mμ Ltiwell dishes and isopropanol is added. Subsequently, 0.5 mg of magnetic silica beads (MagPrep basic, Merck Millipore) is added to the wells which are left gently shaking for 10 min.
3. Washing of the beads: the beads are removed with a magnetic support and the remaining solution is discarded. The beads are then washed three times with 85% ethanol and then left drying to remove residual ethanol.
4. Elution of sRNA: bound sRNA is removed from the beads with 60 μl of pre-heated RNAse-free water.

Protocol Optimisation

Step 1: Varying LB buffer pH

Conditions used: BEP with 60% isopropanol final concentration and LB with different pH (pH 5-10) (see FIG. 2).

TABLE 1

Amount of sRNA extracted from mushroom using LB with pH:

| pH of Lysis Buffer | sRNA extracted (ug/gDW) |
| --- | --- |
| 5 | n.d. |
| 6 | 2 |
| 7 | 5 |
| 7.5 | 50 |
| 8 | 80 |
| 8.5 | 100 |
| 9 | 5 |
| 9.5 | n.d. |
| 10 | n.d. |

The highest yield of sRNA was obtained using a LB with pH 8.5

Step 2: Varying SDS concentrations in the LB.

Conditions used: BEP with 60% isopropanol final concentration and LB at pH 8.5 and various SDS concentration (0-6%) (see FIG. 3).

TABLE 2

Amount of sRNA extracted from mushroom tissue using various SDS concentrations in the LB:

| SDS concentration in LB | sRNA extracted (ug/gDW) |
| --- | --- |
| 0% | 20 |
| 2% | 80 |
| 4% | 65 |
| 6% | 30 |

The highest yield of sRNA was obtained with 2% SDS concentration in the LB

Step 3: Varying NaCl concentration in the LB.

Conditions used: BEP with 60% isopropanol final concentration and LB at pH8.5, 2% SDS and different NaCl concentrations (0-0.3M) (see FIG. 4)

TABLE 3

Amount of sRNA extracted from mushroom tissue using various NaCL concentrations:

| NaCl concentration in LB | sRNA extracted (ug/gDW) |
| --- | --- |
| 0M | 20 |
| 0.1M | 70 |
| 0.2M | 100 |
| 0.3M | 90 |

The highest yield of sRNA was obtained with 0.2M NaCl in the LB

Step 4: Varying EDTA concentration in the LB.

Conditions used: BEP with 60% isopropanol final concentration and LB at pH8.5, 2% SDS, 0.2 M NaCl and different EDTA concentrations (0.20 mM) (see FIG. 5).

TABLE 4

Amount of sRNA extracted from mushroom tissue using various EDTA concentrations in the LB:

| EDTA concentration in LB | sRNA extracted (ug/gDW) |
| --- | --- |
| 0M | n.d. |
| 10 mM | 100 |
| 20 mM | 100 |

The highest yield of sRNA was obtained with 10 or 20 mM EDTA concentration in the LB.

Optimized extraction protocol (OEP):

1. Extraction of sRNA: 100mg of mushroom tissue (fruit body of Agaricus bisporus) is incubated with 200 μL of pre-heated (55° C.) lysis buffer (LB: 50 mM Tris-HCl (pH 8.5) containing 0.2M NaCl, 10 mM EDTA and 2% SDS) at room T for 10 min. with vortexing (30 sec. every 2 min)
2. Binding of sRNA to magnetic beads: after centrifugation, the extract (200 μL) is transferred to mμLtiwell dishes and 300 μL isopropanol (100%) is added. Subsequently, 0.5 mg of magnetic silica beads (MagPrep basic, Merck Millipore) is added to the wells which are left gently shaking for 10 min.
3. Washing of the beads: the beads are removed with a magnetic support and the remaining solution is discarded. The beads are then washed three times with 85% ethanol and then left drying to remove residual ethanol.
4. Elution of sRNA: bound sRNA is removed from the beads with 60 μL of pre-heated RNAse-free water.

With this OEP, a yield of 100 μg/g FW small RNA from Agaricus bisporus is obtained.

MRG Extraction Method

Extraction Buffer

| Tris-HCl | 50 mM pH 8.5 |
| --- | --- |
| NaCl | 0.2M |
| EDTA | 10 mM pH 8.5 |
| SDS | 2% v/v |

1) Place 100 mg of tissue finely grounded tissue (liquid nitrogen) in a 2 ml vessel
2) Add extraction pre-heated (55° C.) buffer (200 μl) and mix vigoroulsy (vortex)
3) Incubate (10', RT) in thermomixer with a shaking regime of 10" every 2' at 400 RPM
4) Spin ((10' @ 9300 RCF, RT)
5) Transfer the supernatant in una new 2 ml vessel
6) Add isopropanol (300 μl ) and mix
7) Add 15 mg di silica gel (Sigma S-5631, prewashed x 2 in DW and incubated O/N with 0.1M HCl) and mix
8) Incubate 10' at RT with gentle shaking
9) Spin (10' @ 9300 RCF, RT)
10) Discard the supernatant and add 500 μl 85% EtOH. Mix gently
11) Spin (5' @ 9300 RCF, RT)
12) Repeat×2 step 10 -11
13) Discard the supernatant and allow the silica gel to dry up.
14) Add 60 μl DW
15) Spin (5' @ 9300 RCF, RT) and collect the supernatant Comparison Between Known Extraction Methods and the Method of the Invention Here inventors compare extraction efficiency and purity of the final extract between the MRG extraction method and other protocols which contain compounds that can aid the purifications of the sRNA fraction such as NaBO4 (Borax) or CTAB which bind to polymeric molecules such as polysaccharides, proteins and DNA or LiCl which at high concentrations (≥2M) precipitate high molecular weight nucleic acids (RNA and DNA) species above 150 bps. The method of the invention is a scalable, inexpensive and safe method for the industrial production of sRNAs extracts for the food industry. All existing protocols have been modified to remove highly toxic compounds and minimize the number purification steps.

Here is a list of the methods used:

Modified CTAB Method (Gambino, G., Perrone, I. and Gribaudo, I. (2008), *A Rapid and effective method for RNA extraction from different tissues of grapevine and other woody plants. Phytochem. Anal.*, 19: 520-525)

Extraction Buffer Composition

| CTAB | 2% (w/v) |
| --- | --- |
| EDTA | 20 mM pH 8.5 |
| NaCl | 1.4M |
| Tris-HCl | 100 mM pH 8.5 |
| PVP | 25% (w/v) |

1) Place 150 mg of tissue finely grounded tissue (liquid nitrogen) in a 1.5 ml vessel
2) Add pre-heated (65° C.) extraction buffer (600 μl) and mix vigorously (vortex)
3) Incubate (65° C., 10') in thermomixer with a shaking regime of 20" every 2' at 400 RPM
4) Spin (10' @ 9300 RCF, 18° C.)
5) Transfer supernatant to a new 1.5 ml vessel
6) Add a volume of 5M NaCl solution to reach 0.5M final NaCl concentration and mix
7) Add a volume of 8M LiCl solution to reach a 2M final LiCl concentration and mix
8) Incubate (4° C., 3.5 h)
9) Spin (15' @ 16500 RCF, 4° C.)
10) Transfer the supernatant to a new 2 ml vessel
11) Add a volume of 3M NaAc solution (pH 5.2) to reach a 0.3M final NaAc concentration and mix.
12) Add an equal volume of isopropanol (50% v/v) and mix
13) Incubate in ice-cold water for 1 h
14) Spin (15' @ 16500 RCF, 4° C.)
15) Discard the supernatant and resuspend the pellet in 500 μl 80% EtOH 16) Spin (15' @ 16500 RCF, 4° C.)
17) Discard the supernatant and allow the pellet to dry up
18) Add DW (50 µl)

LiCl Method (modified from "Rosas-Cárdenas, F. de F., Escobar-Guzmán, R., Cruz-Hernández, A., Marsch-Martinez, N., & de Folter, S. (2015). *An efficient method for miRNA detection and localization in crop plants. Frontiers in Plant Science*, 6, 99)

Extraction Buffer

| Tris-HCl | 100 mM, pH 8.5 |
|---|---|
| SDS | 1% (w/v) |
| LiCl | 100, mM |
| EDTA | 10 mM, pH 8.5 |

1) Place 100 mg of tissue finely grounded tissue (liquid nitrogen) in a 2 ml vessel
2) Add extraction buffer (500 µl) and mix vigorously (vortex)
3) Incubate (60° C., 10') in thermomixer with a shaking regime of 20" every 2' at 400 RPM
4) Spin (10' @ 9300 RCF, 4° C.)
5) Transfer the supernatant to a new 2 ml vessel
6) Add 2M Add a volume of KCl 2M solution to reach 0.55 M final KCl concentration
7) Add a volume of PEG 8000 (50% w/v) solution equal to ⅛ of final volume and mix.
8) Incubate 10' in ice-cold water
9) Add a volume of a 8M LiCl solution to reach 2M final LiCl concentration
10) Incubate 30' in ice-cold water
11) Spin (10' @ 9300 RCF, 4° C.)
12) Transfer the supernatant to a new vessel
13) Add a volume of 3M NaAc solution (pH 5.2) to reach 0.5M final NaAc concentration
14) Add 2 volumes of EtOH and mix
15) Incubate overnight at −20° C.
16) Spin ((15' @ 16500 RCF, 4° C.)
17) Discard the supernatant and resuspend pellet in 600 µl 80% EtOH
18) Spin (10' @ 16500 RCF,)4°)
19) Discard the supernatant and allow the pellet to dry up
20) Add DW (50 µl)

XT Method (Moser, C., Gatto, P., Moser, M., Pindo and Velasco, R. *Isolation of functional RNA from small amounts of different grape and apple tissues. Mol Biotechnol* (2004) 26:95).

Extraction Buffer

| NaBO4 * 10 H2O | 0.2M |
|---|---|
| EDTA | 30 mM |
| SDS | 1% v/v |

Adjust to pH 9.0
Just before use add PVP40 (2% w/v final concentration) and Tween 20 (1% v/v final concentration)
1) Place 100 mg of tissue finely grounded tissue (liquid nitrogen) in a 2 ml vessel
2) Add extraction pre-heated (65° C.) buffer (300 µl) and mix vigoroulsy (vortex)
3) Incubate (65° C., 10') in thermomixer with a shaking regime of 20" every 2' at 400 RPM
4) Spin (10' @ 9300 RCF, 4° C.)
5) Transfer the supernatant to a new 1.5 mL vessel
6) Add a volume of a 5M NaCl solution to reach 0.5M final NaCl concentration and mix
7) Add a volume of 8M LiCl solution to reach 2M final LiCl concentration
8) Incubate 3 h at 4° C.
9) Spin (15' @ 16500 RCF, 4° C.)
10) Transfer the supernatant to a new 1.5 mL vessel)
11) Add a volume of 3M NaAc3M solution (pH 5.2) to reach 0.3M final NaAc concentration and mix
12) Add 1 volume of isopropanol and mix vigorously
13) Incubate 1 h in ice-cold water
14) Spin (15' @ 16500 RCF, 4° C.)
15) Discard the supernatant and wash the pellet with 500 µl 80% EtOH
16) Spin (10' @ 16500 RCF, 4° C.)
17) Discard the supernatant and allow the pellet to dry up
18) Add DW (50 µl)

TABLE 5 sRNA yield obtained with the above described methods:

| | LiCl | CTAB | XT | MRG |
|---|---|---|---|---|
| Bean mature cotyledons | 275 ± 38 | 41 ± 21 | 163 ± 54 | 533 ± 69 |
| Pea cotyledons | 164 ± 51 | 9 ± 7 | 371 ± 48 | 774 ± 56 |
| Peppermint leaves (fresh) | 66 ± 11 | 78 ± 14 | 98 ± 12 | 125 ± 75 |
| Peppermint leaves (dry) | 133 ± 23 | 106 ± 15 | 125 ± 30 | 572 ± 129 |
| Soybean sprouts | 120 ± 20 | 87 ± 9 | 125 ± 20 | 314 ± 41 |
| Carrot root | 24 ± 4 | 5 ± 5 | 45 ± 5 | 19 ± 11 |
| Calendula flowers | 77 ± 11 | 116 ± 77 | 80 ± 8 | 110 ± 10 |
| Onion bulb | 32 ± 4 | 6 ± 4 | 23 ± 13 | 59 ± 16 |
| Mushrooms (Champignon) | 67 ± 10 | 55 ± 11 | 100 ± 10 | 146 ± 11 |
| Cumin seed | 12 ± 7 | 5 ± 3 | 24 ± 9 | 24 ± 8 |
| Apple fruiting | 5 ± 5 | 20 ± 6 | 8 ± 4 | 27 ± 9 |

Table 5. Total sRNA extracted from different tissues of plants and fungi using different extraction methods. The sRNA content of the final extract was determined using the Agilent RNA 6000 Nano Kit through the Bioanalyzer instrument/Agilent Technologies) and data are expressed as ug/g of tissue ± S.D.

MRG Method Scale up to 1 Kg Range

The matrix chosen to setup the scale up of the MRG method was composed by the fruiting bodies (caps and stalks) of "champignon" mushrooms or mature cotyledons of beans or peas.

1 Kg of plant or mushroom tissue was snap frozen in liquid nitrogen and ground to a fine powder using the TissueLyser II (Qiagen) with titanium jars and 10 mm diameters titanium spheres. Jars and spheres were kept cold with liquid nitrogen. The grinding time was set to 1 minute at a shake frequency of 30 Hz.

The tissue was then placed in a 3 L becker and 2 L of pre-heated (55° C.) and MRG Lysis Buffer (LB) was slowly added and thoroughly mixed to homogenize the material. The solution was kept under gentle agitation for 10 minutes.

The homogenate was then filtered through cellulose sheets and the resulting liquid was transfered to a 5 L tank to which 1.5 volumes of 100% isopropanol were added. After agitation to homogenize the solution, 100 gr of silicon dioxide beads, ⁵⁰⁄₇₀ mesh particle size (Sigma S-5631) were added and the tank was kept under agitation for 10 minutes. The beads were prewashed ×2 in DW and incubated O/N with 0.1M HCl prior to use.

After allowing sedimentation of the beads, the liquid phase was removed and the beads were washed 3 times with 400 ml EtOH 85% which was added to the beads and left in the tank with agitation for 10 minutes.

After the final wash the silicon dioxide was allowed to dry and then sRNAs were eluted with 200 mL of pre-heated (65° C.) water.

TABLE 6

Total sRNA extracted from 1 Kg of plants and fungal tissue using the MRG extraction method. The sRNA content of the final extract was determined using the Agilent RNA 6000 Nano Kit through the Bioanalyzer instrument/Agilent Technologies) and data are expressed as mg/Kg of tissue ± S.D.

| TISSUE | sRNA yield (mg/Kg) |
|---|---|
| Bean mature cotyledons | 475 ± 78 |
| Pea mature cotyledons | 564 ± 59 |
| Mushrooms (champignon) fruiting body | 116 ± 31 |

Extraction of sRNAs from Plant or Mushroom Tissues Without Tissue Homogenisation A method for the extraction of sRNA from plant and mushroom tissues without tissue homogenization was also developed. Intact or coarsely chopped plant or mushroom tissues (100 mg) were pre-incubated for 16 h at 4° C. in 8.75 mM $NaHCO_3$. Subsequently, after removal of the washing liquid, the tissues were placed in vessels containing 1 L of various extraction media: MRG LB (with exclusion of SDS), water or 30 mM $NaHCO_3$, and incubated at 60° C. or 95° C. (boiling) and the sRNA present in the liquid phase measured using the MRG method (from step 5). For incubation at 60° C. the liquid phase was exchanged every 60 min. and the total duration was 180 min. For incubation at 95° C., the volume was kept constant by topping up and the whole duration was 60 min.

TABLE 7

| | Extraction treatment | | | |
|---|---|---|---|---|
| | MRG LB | WATER | $NaHCO_3$ | |
| TISSUE | 95° C. | 95° C. | 60° C. | 95° C. |
| Bean cotyledons | 103 ± 19 | 87 ± 24 | 125 ± 21 | 447 ± 51 |
| Pea cotyledons | 6 ± 2 | 24 ± 7 | 40 ± 15 | 363 ± 53 |
| Peppermeant leaves (fresh) | 6 ± 2 | 15 ± 2 | 7 ± 2 | 33 ± 5 |
| Peppermeant leaves (dry) | 75 ± 21 | 54 ± 11 | 170 ± 22 | 170 ± 11 |
| Soybean sprouts | nd | 2 ± 1 | nd | 3 ± 2 |
| Carrot root | nd | 4 ± 2 | 2 ± 1 | 15 ± 5 |
| Calendula flowers | nd | 3 ± 2 | nd | 7 ± 2 |
| Onion bulb | 5 ± 1 | 6 ± 2 | 2 ± 0.5 | 6 ± 2 |
| Mushrooms (Champignon) | 52 ± 8 | 6 ± 2 | nd | 55 ± 10 |
| Cumin seed | 30 ± 6 | 15 ± 4 | 37 ± 7 | 120 ± 22 |
| Apple fruit | 4 ± 2 | 5 ± 2 | 10 ± 3 | 7 ± 2 |

Table 7. Total sRNA extracted from 100 g of plants and fungal tissue incubated with extraction media without tissue homogenization. The total sRNA content of the liquid extract was determined using the Agilent RNA 6000 Nano Kit through the Bioanalyzer instrument/Agilent Technologies) and data are expressed as ug/g of tissue ± S.D.

This process allows to reduce costs and, after extraction of sRNAs, the plant biomass may be reused in the food chain and not becoming industrial waste.

Further Treatment of Final sRNA Extract

The final extract may be concentrated through water removal (vacuum-drying) or filtration through size exclusion membranes (must retain 13 KDa molecules).

1. RNAse

In order to improve the biological efficacy of the concentrated sRNA extracts, a method for reducing the possibility of off-target sequence-dependent or RISC-mediated interference and/or pro-inflammatory activity of ssRNA molecules with length above 40 nt. was developed. Concentrated sRNA extracts were incubated with RNAse A (0.02 μg/10 μl extract) in the presence of 0.4M NaCl for 30 minutes at RT. With this treatment 60%-90% of sRNA are removed and the resulting extract was highly enriched with dsRNA molecular species 2. dsRNA purification via dsRNA binding motifs (dsRBMs)

In order to improve the biological efficacy of the concentrated sRNA extracts, a method for reducing the possibility of off-target sequence-dependent or RISC-mediated interference and/or pro-inflammatory activity of ssRNA molecules with length above 40 nt. was developed. RNA biding proteins (RBP) abund in nature and are able to selectively and reversibly bind to RNAs.

This ability is provided by specific RNA binding domains (RBDs) which exists in various forms. In particular, the double stranded RNA binding domain (dsRBM) is a 70-75 amino-acid domain which plays a critical role in RNA processing, RNA localization, RNA interference, RNA editing, and translational repression. The dsRBMs interacts along the RNA duplex via both α-helices and β1-β2 loop and make contact with the sugar-phosphate backbone of the major groove and of one minor groove, which is mediated by the β01-β02 loop along with the N-terminus region of the alpha helix 2. This interaction is a unique adaptation for the shape of an RNA double helix as it involves 2'-hydroxyls and phosphate oxygen. Despite the common structural features among dsRBMs, they exhibit distinct chemical frameworks, which permits specificity for a variety for RNA structures including stem-loops, internal loops, bulges or helices containing mismatches. The Carnation Italian ringspot virus (CIRV) 19 kDa protein (p19), which contains a basic aminoacid signature that favor RNA binding, acts as a dimer and binds with high affinity (nM-pM range) and little sequence-specificity to the minor groove of siRNA duplexes of selectively 21-25 nt. When p19 siRNA Binding Protein is expressed in plants it suppresses RNA interference.

Treatment of concentrated sRNA extracts (10 ug) with 200 U p19 siRNA binding proteins (product number M0310S NewEngland BioLabs) using the protocol indicated in the Company datasheet (M0S10) resulted in removal of 95% of sRNA and purification of 21-24 nt dsRNA. This method can also be applied to the dsRNA enriched extracts following RNAse treatment (see above).

The invention claimed is:

1. A method for isolating a fraction enriched of small RNA molecules from a fungal and/or plant sample, comprising:
   a') incubating fungal and/or plant tissue or cells with an alkali metal bicarbonate solution at a temperature of 50-100° C., separating the liquid from the solid phase to obtain a liquid phase;
   b) adding an alcohol solution to the liquid phase obtained in step a') to obtain a solution;
   c) loading the obtained solution to a solid support able to selectively bind small RNA molecules; and
   d) eluting small RNA molecules from said solid support.

2. The method of claim 1, wherein the bicarbonate solution is a diluted bicarbonate solution.

3. The method of claim 1, further comprising after step a'), a step a") wherein the liquid phase is discarded and a diluted bicarbonate solution is added at a temperature of 60-100° C. and wherein the diluted bicarbonate solution is a 5-10 mM NaHCO$_3$ solution.

4. The method of claim 1, wherein the temperature of the bicarbonate solution is about 95° C.

5. The method of claim 1, wherein before step a') fungal and/or plant tissue or cells are incubated with a diluted bicarbonate solution at 0-10° C. and wherein the diluted bicarbonate solution is a 5-10 mM NaHCO$_3$ solution.

6. The method of claim 1, wherein the alcohol is isopropanol, ethanol or any alcohol able to reduce the activity of water and therefore the salvation of sRNAs and promote their binding to the solid support.

7. The method of claim 1, wherein the alcohol solution comprises isopropanol at a final concentration of 60% v/v.

8. The method of claim 1, wherein the small RNA molecules are eluted from the solid support with RNAse-free water, and/or wherein the small RNA molecules are eluted from the solid support at a temperature of about 50° C. to about 100° C.

9. The method of claim 1, wherein the solid support is a mineral support or polymer support.

10. The method of claim 1, further comprising capturing the eluted small RNA molecules.

11. The method of claim 1, further comprising:
step e) selectively removing ssRNAs with RNAse treatment from the eluted small RNA molecules and/or
step f) treating the eluted small RNA molecules with an agent which binds with high affinity to siRNA duplexes of selectively 21-25 nt, to enrich the 21-24 bp dsRNA fraction.

12. The method of claim 1, wherein the small RNA molecules include miRNA, siRNA, snRNA, snoRNA, and/or tRNA molecules and, preferably the small RNA molecules consisting of at most 100 nucleotides.

13. The method of claim 1, wherein the small RNA molecules are in the single stranded and/or double stranded configurations, and/or wherein said the small RNA molecules are characterized by the presence of a phosphate group at the 5' ends or a methyl group at the 3' ends, and/or wherein the small RNA molecules are miRNA, mature miRNA and/or siRNA molecules.

14. The method of claim 2, wherein the diluted bicarbonate solution is a 5-100 mM NaHCO$_3$ solution.

15. The method of claim 2, wherein the diluted bicarbonate solution is a 30 mM NaHCO$_3$ solution.

16. The method of claim 3 wherein the diluted bicarbonate solution is a 8.75 mM NaHCO$_3$ solution.

17. The method of claim 3 wherein step a") is repeated.

18. The method of claim 4, wherein the temperature of the bicarbonate solution is 100° C.

19. The method of claim 4, wherein the temperature of the bicarbonate solution is 60° C.

20. The method of claim 5, wherein before step a') fungal and/or plant tissue or cells are incubated with a diluted bicarbonate solution at 4° C.

21. The method of claim 5, wherein the diluted bicarbonate solution is an 8.75 mM NaHCO$_3$ solution.

22. The method of claim 8, wherein the small RNA molecules are eluted from the solid support at a temperature of about 55° C. to about 65° C.

23. The method of claim 12, wherein the small RNA molecules consisting of between 21 and 24 nucleotides.

* * * * *

UNITED STATES PATENT AND TRADEMARK OFFICE
CERTIFICATE OF CORRECTION

PATENT NO. : 11,111,488 B2
APPLICATION NO. : 15/770008
DATED : September 7, 2021
INVENTOR(S) : Viola et al.

It is certified that error appears in the above-identified patent and that said Letters Patent is hereby corrected as shown below:

In the Claims

In Column 25, Line 12, "salvation of sRNAs" in Claim 6 should read:
--6. The method of claim 1, wherein the alcohol is isopropanol, ethanol or any alcohol able to reduce the activity of water and therefore the solvation of sRNAs and promote their binding to the solid support.--

In Column 26, Lines 5-7, "said the small" in Claim 13 should read:
--and/or wherein the small RNA molecules are characterized by the presence of a phosphate group at the 5' ends or a methyl group at the 3' ends,--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*